United States Patent
Matsumura et al.

(10) Patent No.: US 11,844,847 B2
(45) Date of Patent: Dec. 19, 2023

(54) SULFUR-CONTAINING POLYMERIZABLE MONOMER AND USE THEREOF

(71) Applicants: SUN MEDICAL CO., LTD., Moriyama (JP); MITSUI CHEMICALS, INC., Tokyo (JP)

(72) Inventors: Hideo Matsumura, Tokyo (JP); Sayaka Miyamori, Moriyama (JP); Takashi Yamamoto, Moriyama (JP); Kazuhiko Yoshinaga, Moriyama (JP); Shigeru Mio, Chiba (JP); Shinji Kiyono, Kimitsu (JP); Hina Suzuki, Chiba (JP)

(73) Assignees: SUN MEDICAL CO., LTD., Moriyama (JP); MITSUI CHEMICALS, INC., Tokyo (JP)

( * ) Notice: Subject to any disclaimer, the term of this patent is extended or adjusted under 35 U.S.C. 154(b) by 78 days.

(21) Appl. No.: 17/265,945

(22) PCT Filed: Aug. 9, 2019

(86) PCT No.: PCT/JP2019/031707
§ 371 (c)(1),
(2) Date: Feb. 4, 2021

(87) PCT Pub. No.: WO2020/032268
PCT Pub. Date: Feb. 13, 2020

(65) Prior Publication Data
US 2021/0298997 A1    Sep. 30, 2021

(30) Foreign Application Priority Data

Aug. 9, 2018   (JP) ................ 2018-150309

(51) Int. Cl.
| A61K 6/30 | (2020.01) |
| A61K 6/76 | (2020.01) |
| A61K 6/62 | (2020.01) |
| C07D 233/86 | (2006.01) |
| C07D 251/46 | (2006.01) |
| C09J 133/12 | (2006.01) |

(52) U.S. Cl.
CPC ........... *A61K 6/30* (2020.01); *A61K 6/62* (2020.01); *A61K 6/76* (2020.01); *C07D 233/86* (2013.01); *C07D 251/46* (2013.01); *C09J 133/12* (2013.01)

(58) Field of Classification Search
CPC ..................................... A61K 6/887
See application file for complete search history.

(56) References Cited

U.S. PATENT DOCUMENTS

| 4,525,493 A | 6/1985 | Omura et al. |
| 4,539,382 A | 9/1985 | Omura et al. |
| 4,612,384 A | 9/1986 | Omura et al. |
| 4,650,847 A | 3/1987 | Omura et al. |
| 4,755,620 A | 7/1988 | Iwamoto et al. |
| 5,288,341 A | 2/1994 | Kojima et al. |
| 5,795,497 A | 8/1998 | Kimura et al. |
| 2019/0240117 A1 | 8/2019 | Kishi et al. |

FOREIGN PATENT DOCUMENTS

| JP | S54-21438 A | 2/1979 |
| JP | S58-21607 A | 2/1983 |
| JP | S59-140276 A | 8/1984 |
| JP | S59-142268 A | 8/1984 |
| JP | S61-293951 A | 12/1986 |
| JP | S64-83254 A | 3/1989 |
| JP | H01-138282 A | 5/1989 |
| JP | H04-217905 A | 8/1992 |
| JP | H05-117595 A | 5/1993 |
| JP | H08-113763 A | 5/1996 |
| JP | H10-1409 A | 1/1998 |
| JP | 2008-056649 A | 3/2008 |
| WO | WO-2009142720 A1 * | 11/2009 ............. A01N 43/50 |
| WO | 2018/034212 A1 | 2/2018 |

OTHER PUBLICATIONS

Database Registry, Apr. 30, 2018, RN 2221947-53-9, Retrieved from SIN International [online]; retrieved on Oct. 10, 2019. (1 page).
International Search Report dated Oct. 21, 2019, by the Japanese Patent Office in corresponding International Patent Application No. PCT/JP2019/031707 and an English translation of the Report. (5 pages).
Written Opinion of the International Searching Authority dated Oct. 21, 2019, by the Japanese Patent Office in corresponding International Patent Application No. PCT/JP2019/031707 and an English translation of the Opinion. (7 pages).
Babich, et al., "Synthesis of benzylidene and azo containing polymers for photophysical application", French-Ukrainian Journal of Chemistry, 2013, vol. 1, No. 1, pp. 105-110.
Extended European Search Report dated Mar. 17, 2022, for corresponding EP patent application No. 19847149.2.

* cited by examiner

*Primary Examiner* — Michael F Pepitone
(74) *Attorney, Agent, or Firm* — BUCHANAN INGERSOLL & ROONEY PC

(57) ABSTRACT

A compound (A) is represented by the formula (1):

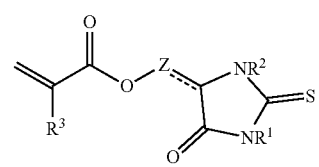

wherein $R^1$ is a hydrogen atom or an alkali metal atom, $R^2$ is a hydrogen atom or an alkali metal atom, $R^3$ is a hydrogen atom or a methyl group, Z is a divalent or trivalent organic group, and the lines consisting of a solid line and a broken line bonded to Z represent a single bond or a double bond.

8 Claims, No Drawings

SULFUR-CONTAINING POLYMERIZABLE MONOMER AND USE THEREOF

CROSS-REFERENCE TO RELATED APPLICATIONS

This application is a national stage application of International Application No. PCT/JP2019/031707, filed on Aug. 9, 2019, which claims priority from Japanese Patent Application No. 2018-150309, filed on Aug. 9, 2018. The above applications are expressly incorporated herein by reference, in their entireties.

TECHNICAL FIELD

The present invention relates to sulfur-containing polymerizable monomers and use thereof.

BACKGROUND ART

In oral surgeries and dental clinics, it is a routine practice to bond, to the tooth substances, prostheses such as metal inlays, onlays, crowns and bridges, posts and cores of abutment teeth, or orthodontic brackets. Dental adhesive materials disclosed in Patent Literature 1 and Patent Literature 2 that contain a phosphoric acid ester monomer or a carboxylic acid monomer are practically used as adhesive materials for bonding metals to the tooth substances. Before a dental metal is bonded through the adhesive material, the bonding surface of the dental metal is preliminarily roughened by sandblasting to enhance the adhesion.

Noble metals such as gold, silver, platinum and palladium, and noble metal alloys principally containing these noble metals are sandblasted to roughen the bonding surface of the noble metals or the alloys thereof, and thereafter the surface is further treated by, for example, tin plating or thermal oxidation. However, tin plating and thermal oxidation treatment are laborious. Further, sufficiently durable adhesion cannot be obtained even when such a pretreatment is performed. An approach to addressing this problem is to apply a primer to the bonding surface of a noble metal or an alloy thereof. For example, Patent Literatures 3 to 6 disclose primers that contain a polymerizable compound having a functional group such as a thiophosphoric acid group, a thiophosphoryl chloride group, a triazinedithione derivative or a mercaptothiadiazole derivative. These primers are applied to noble metals or alloys thereof to simplify the operation and to enhance the adhesion.

CITATION LIST

Patent Literature

Patent Literature 1: JP-A-S58-21607
Patent Literature 2: JP-A-S61-293951
Patent Literature 3: JP-A-H01-138282
Patent Literature 4: JP-A-H05-117595
Patent Literature 5: JP-A-S64-83254
Patent Literature 6: JP-A-H08-113763

SUMMARY OF INVENTION

Technical Problem

Unfortunately, if the sulfur-containing polymerizable monomer has low solubility with respect to a solvent, the primer that is obtained contains a low concentration of the sulfur-containing polymerizable monomer and does not offer high adhesion when applied to a noble metal or an alloy thereof. Further, increasing the concentration of the sulfur-containing polymerizable monomer requires that more solvent be contained in the composition and thus results in a decrease in the amounts of other polymerizable monomers, possibly leading to low adhesion.

In light of the circumstances discussed above, an object of the present invention is to provide a compound that has excellent solubility with respect to solvents and is suited for bonding applications.

Solution to Problem

As a result of studies directed to achieving the above object, the present inventors have found that the problems discussed above can be solved with a sulfur-containing polymerizable monomer having a structure described below, thus completing the present invention. For example, the present invention pertains to the following [1] to [15].

[1] A compound (A) represented by the formula (1):

[Chem. 1]

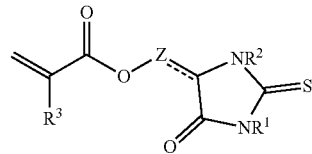

(1)

wherein $R^1$ is a hydrogen atom or an alkali metal atom, $R^2$ is a hydrogen atom or an alkali metal atom, $R^3$ is a hydrogen atom or a methyl group, Z is a divalent or trivalent organic group, and the lines consisting of a solid line and a broken line bonded to Z represent a single bond or a double bond.

[2] The compound (A) described in [1], wherein the molecular weight is 200 to 600.

[3] The compound (A) described in [1] or [2], wherein the topological polar surface area (tPSA) is not less than 50.00 Å$^2$.

[4] The compound (A) described in [3], wherein the C log P value is not less than −5.000.

[5] The compound (A) described in any of [1] to [4], which is not a compound represented by the following formula:

[Chem. 2]

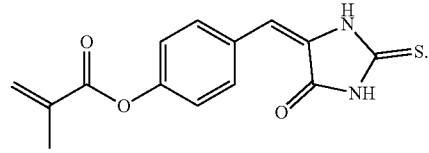

[6] The compound (A) described in any of [1] to [5], wherein the divalent or trivalent organic group Z in the formula (1) includes one or more groups selected from divalent groups represented by the formula (Z1), ether bonds, 1,4-phenylene groups, 1,4-cyclohexylene groups and divalent linear saturated hydrocarbon groups,

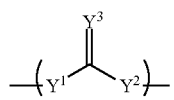

(Z1)

wherein $Y^1$ and $Y^2$ are each independently an oxygen atom, a divalent group represented by —$CH_2$— or a divalent group represented by —NH—, and $Y^3$ is an oxygen atom or a sulfur atom.

[7] The compound (A) described in any of [1] to [6], wherein the divalent or trivalent organic group Z in the formula (1) is a C6-C20 linear saturated hydrocarbon group or a C6-C20 group having —O—C(=O)—$CH_2$—.

[8] An adhesive composition including the compound (A) described in any of [1] to [7].

[9] The adhesive composition described in [8], which is for medical or dental use.

[10] The adhesive composition described in [8] or [9], further including at least one component selected from radically polymerizable monomers (B) other than the compounds (A), silane coupling agents (C), fillers (D), polymerization initiators (E), reducing compounds (F), organic solvents (G) and waters (H).

[11] The adhesive composition described in any of [8] to [10], wherein the adhesive composition further includes a radically polymerizable monomer (B) other than the compound (A), and the proportion of the compound (A) is 0.01 to 30 mass % of the total of the compound (A) and the radically polymerizable monomer (B) taken as 100 mass %.

[12] The adhesive composition described in any of [8] to [11], which is a medical or dental primer composition.

[13] The adhesive composition described in any of [8] to [12], wherein the total proportion of an organic solvent (G) and water (H) in the adhesive composition is 5 to 99.5 mass %.

[14] The adhesive composition described in any of [8] to [13], wherein the proportion of the compound (A) in the adhesive composition is 0.01 to 30 mass %.

[15] A cured product obtained by curing the adhesive composition described in any of [8] to [14].

Advantageous Effects of Invention

The compounds provided according to the present invention exhibit excellent solubility with respect to solvents and are suited for bonding applications.

DESCRIPTION OF EMBODIMENTS

Hereinbelow, embodiments of the present invention will be described.

In the present specification, the term "(meth)acrylic" indicates acrylic or methacrylic and, for example, "(meth) acrylic acid" means methacrylic acid or acrylic acid. Similarly, the term "(meth)acryloyl" indicates "acryloyl" or "methacryloyl", and the term "(meth)acrylate" indicates "acrylate" or "methacrylate".

In the present specification, the numerical ranges indicated with "to" include the values before and after the "to" as the minimum value and the maximum value, respectively.

In the numerical ranges described stepwise in the present specification, an upper limit value or a lower limit value for a given numerical range may be replaced with an upper limit value or a lower limit value of another numerical range in the stepwise description. Further, in the numerical ranges described in the present specification, an upper limit value or a lower limit value for a given numerical range may be replaced with a value described in EXAMPLES.

Components illustrated in the present specification, for example, components in an adhesive composition may be each a single component or a combination of two or more components unless otherwise mentioned.

[Compounds (A)]

A compound (A) of the present invention is represented by the formula (1).

The compound (A) is a polymerizable monomer that includes both, in the molecule, a thiohydantoin skeleton which holds promise of showing adhesion, and also effectively enhancing the adhesion, with respect to noble metals and noble metal alloys, and a (meth)acrylate skeleton which offers enhanced solubility with respect to known organic solvents and radically polymerizable monomers. Thus, the compound (A) exhibits excellent solubility with respect to organic solvents and radically polymerizable monomers.

[Chem. 4]

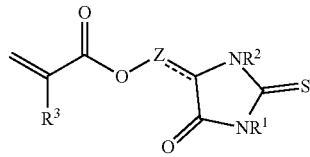

(1)

In the formula (1), $R^1$ is a hydrogen atom or an alkali metal atom, $R^2$ is a hydrogen atom or an alkali metal atom, and $R^3$ is a hydrogen atom or a methyl group. Examples of the alkali metal atoms include lithium, sodium and potassium.

Z is a divalent or trivalent organic group, and the lines (the double line) consisting of a solid line and a broken line bonded to Z represent a single bond or a double bond. In the organic group represented by Z, the atom bonded to —C(=O)—O— in the formula (1) is preferably a carbon atom. Further, in the organic group represented by Z, the atom bonded to the thiohydantoin skeleton in the formula (1) is preferably a carbon atom.

When the lines (the double line) consisting of a solid line and a broken line bonded to Z are a single bond, the divalent organic group Z preferably includes one or more groups selected from divalent groups represented by the formula (Z1), ether bonds (—O—), 1,4-phenylene groups, 1,4-cyclohexylene groups and divalent linear saturated hydrocarbon groups.

[Chem. 5]

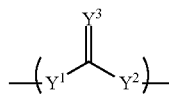

(Z1)

In the formula (Z1), $Y^1$ and $Y^2$ are each independently an oxygen atom, a divalent group represented by —$CH_2$— or a divalent group represented by —NH—, and $Y^3$ is an oxygen atom or a sulfur atom.

Examples of the divalent groups represented by the formula (Z1) include the divalent group represented by —NH—C(=O)—O—, the divalent group represented by —O—C(=O)—CH$_2$—, the divalent group represented by —O—C(=O)—O—, the divalent group represented by —NH—C(=O)—NH—, and the divalent groups resulting from the substitution of the above groups with "=S" in place of "(=O)". From the point of view of solubility, the divalent group represented by —O—C(=O)—CH$_2$— is preferable.

In the case of the divalent group represented by —O—C(=O)—CH$_2$— or —O—C(=S)—CH$_2$—, it is preferable that the divalent group be bonded in such a manner that its —CH$_2$— is directed to the thiohydantoin skeleton side. In the case of the divalent group represented by —NH—C(=O)—O— or —NH—C(=S)—O—, it is preferable that the divalent group be bonded so that its —O— is directed to the thiohydantoin skeleton side.

The divalent organic group represented by Z is preferably a divalent linear saturated hydrocarbon group alone or preferably includes —O—C(=O)—CH$_2$— as the divalent group represented by the formula (Z1).

The number of carbon atoms in the divalent linear saturated hydrocarbon group is usually 1 to 40, preferably 2 to 30, and more preferably 3 to 25. When the divalent organic group represented by Z includes a plurality of divalent linear saturated hydrocarbon groups, the total number of carbon atoms in the divalent linear saturated hydrocarbon groups is preferably within the above range. Examples of the divalent linear saturated hydrocarbon groups include linear alkanediyl groups such as methanediyl group, ethane-1,2-diyl group, propane-1,3-diyl group, butane-1,4-diyl group, hexane-1,6-diyl group, octane-1,8-diyl group, decane-1,10-diyl group, dodecane-1,12-diyl group, tetradecane-1,14-diyl group, hexadecane-1,16-diyl group, octadecane-1,18-diyl group and eicosane-1,20-diyl group; and branched linear alkanediyl groups obtained by adding one or more C1-C4 alkyl groups as side chains to the above linear alkanediyl groups.

Examples of the divalent organic groups Z include:
divalent linear saturated hydrocarbon groups; and
groups having one or more groups selected from divalent groups represented by the formula (Z1), ether bonds (—O—), 1,4-phenylene groups and 1,4-cyclohexylene groups, and a divalent linear saturated hydrocarbon group.

In the divalent organic group Z, the group bonded to —C(=O)—O— in the formula (1) is preferably a divalent linear saturated hydrocarbon group. In the divalent organic group Z, the divalent linear saturated hydrocarbon group bonded to —C(=O)—O— in the formula (1) preferably has 1 to 30 carbon atoms, and more preferably has 2 to 25 carbon atoms. In the divalent organic group Z, the group bonded to the thiohydantoin skeleton in the formula (1) is preferably a divalent linear saturated hydrocarbon group. In the divalent organic group Z, the divalent linear saturated hydrocarbon group bonded to the thiohydantoin skeleton in the formula (1) preferably has 1 to 10 carbon atoms, and more preferably has 1 to 5 carbon atoms. When, for example, the divalent organic group Z has one group selected from a divalent group represented by the formula (Z1), an ether bond (—O—), a 1,4-phenylene group and a 1,4-cyclohexylene group, it is preferable that the group (the divalent group represented by the formula (Z1), the ether bond (—O—), the 1,4-phenylene group or the 1,4-cyclohexylene group) be bonded to the —C(=O)—O— and the thiohydantoin skeleton in the formula (1) each via a divalent linear saturated hydrocarbon group.

When the lines (the double line) consisting of a solid line and a broken line bonded to Z represent a double bond, the trivalent organic group Z may be, for example, a trivalent linear saturated hydrocarbon group; or a group having one or more groups selected from divalent groups represented by the formula (Z1), ether bonds (—O—), 1,4-phenylene groups and 1,4-cyclohexylene groups, and a trivalent linear saturated hydrocarbon group. Here, the term "saturated" in the linear saturated hydrocarbon groups means that the hydrocarbon skeleton has no unsaturated bonds except the double bond bonded to the thiohydantoin skeleton.

When, for example, the trivalent organic group Z has one group selected from a divalent group represented by the formula (Z1), an ether bond (—O—), a 1,4-phenylene group and a 1,4-cyclohexylene group, it is preferable that the group (the divalent group represented by the formula (Z1), the ether bond (—O—), the 1,4-phenylene group or the 1,4-cyclohexylene group) be bonded to the —C(=O)—O— in the formula (1) via a divalent linear saturated hydrocarbon group and be bonded to the thiohydantoin skeleton in the formula (1) via a trivalent linear saturated hydrocarbon group.

When the lines (the double line) consisting of a solid line and a broken line bonded to Z represent a double bond, the moiety of the linear saturated hydrocarbon group that is bonded to the thiohydantoin skeleton is the result of the removal of two hydrogen atoms from the same carbon atom in a linear saturated hydrocarbon, with the free valence constituting the double bond.

The trivalent organic group represented by Z is preferably a trivalent linear saturated hydrocarbon group alone or preferably includes a 1,4-cyclohexylene group, a 1,4-phenylene group or an ether bond (—O—).

The number of carbon atoms in the trivalent linear saturated hydrocarbon group is usually 1 to 40, preferably 2 to 30, and more preferably 3 to 25. When the trivalent organic group represented by Z includes a plurality of linear saturated hydrocarbon groups, the total number of carbon atoms in the linear saturated hydrocarbon groups is usually not more than 40, preferably not more than 30, and more preferably not more than 25.

To attain excellent solubility, the divalent or trivalent organic group represented by Z is preferably a C6-C20 linear saturated hydrocarbon group or a C6-C20 group having —O—C(=O)—CH$_2$—.

The compound (A) is preferably not the compound represented by the following formula:

[Chem. 6]

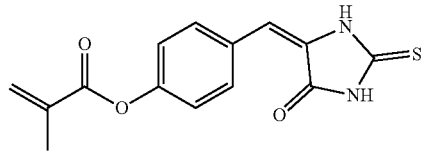

The molecular weight of the compound (A) is preferably 200 to 600, more preferably 240 to 550, and still more preferably 300 to 500.

From the point of view of the solubility into solvents, the topological polar surface area (tPSA) of the compound (A) is preferably not less than 50.00 Å$^2$, and more preferably not less than 60.00 Å². The tPSA of the compound (A) is preferably not more than 200.00 Å², and more preferably not more than 150.00 Å². The tPSA indicates the area of polar portions of the molecular surface.

From the point of view of the solubility into solvents, the C log P value of the compound (A) is preferably not less than −5.000, and more preferably not less than −1.000. The C log P value of the compound (A) is preferably not more than 20.000, and more preferably not more than 10.000. When, in particular, the topological polar surface area (tPSA) of the compound (A) is within the above preferred range, the C log P value of the compound (A) preferably falls in this range.

The C log P value is obtained by calculating the common logarithm of the 1-octanol/water partition coefficient of a chemical substance, and is used as an index of how the chemical substance is hydrophilic or hydrophobic.

tPSA and C log P may be calculated with ChemDraw (registered trademark) Professional (version: 16.0.1.4 (77)).

In an embodiment, the compound (A) is a compound represented by the formula (2):

[Chem. 7]

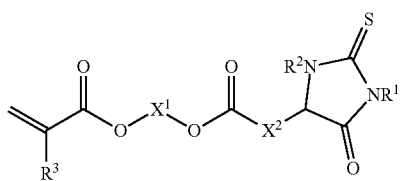

(2)

In the formula (2), $R^1$ is a hydrogen atom or an alkali metal atom, $R^2$ is a hydrogen atom or an alkali metal atom, $R^3$ is a hydrogen atom or a methyl group, $X^1$ is a divalent saturated hydrocarbon group preferably having 2 to 20 carbon atoms, more preferably 4 to 10 carbon atoms, and $X^2$ is a divalent saturated hydrocarbon group preferably having 2 to 6 carbon atoms, more preferably 2 to 4 carbon atoms.

Examples of the alkali metal atoms include lithium, sodium and potassium.

Examples of the divalent saturated hydrocarbon groups having 2 to 20 carbon atoms or 2 to 6 carbon atoms include divalent linear saturated hydrocarbon groups and divalent alicyclic-containing saturated hydrocarbon groups.

Examples of the divalent linear saturated hydrocarbon groups include linear alkanediyl groups such as ethane-1,2-diyl group, propane-1,3-diyl group, butane-1,4-diyl group, hexane-1,6-diyl group, octane-1,8-diyl group, decane-1,10-diyl group, dodecane-1,12-diyl group, tetradecane-1,14-diyl group, hexadecane-1,16-diyl group, octadecane-1,18-diyl group and eicosane-1,20-diyl group; and branched linear alkanediyl groups obtained by adding one or more C1-C4 alkyl groups as side chains to the above linear alkanediyl groups.

The divalent alicyclic-containing saturated hydrocarbon groups are divalent saturated hydrocarbon groups having a saturated aliphatic hydrocarbon ring, and are not necessarily composed solely of a saturated aliphatic hydrocarbon ring and may include a chain structure as a portion thereof. Examples of the saturated aliphatic hydrocarbon rings include monocycles such as cyclobutane ring, cyclohexane ring and cyclodecane ring; and polycycles such as norbornane ring, adamantane ring and tricyclo[5.2.1.0$^{2,6}$]decane ring.

Examples of the divalent alicyclic-containing saturated hydrocarbon groups include divalent saturated aliphatic hydrocarbon rings; divalent linear saturated hydrocarbon groups substituted with a saturated aliphatic hydrocarbon ring described above in place of at least one hydrogen atom; and divalent groups composed of a divalent saturated aliphatic hydrocarbon ring and a divalent linear saturated hydrocarbon group linked to each other.

$X^1$ is preferably a C2-C20 divalent linear saturated hydrocarbon group, and more preferably a C2-C20 linear alkanediyl group. $X^2$ is preferably a C2-C6 divalent linear saturated hydrocarbon group, and more preferably a C2-C6 linear alkanediyl group.

Specific examples of the compounds (A) include the following compounds.

[Chem. 8]

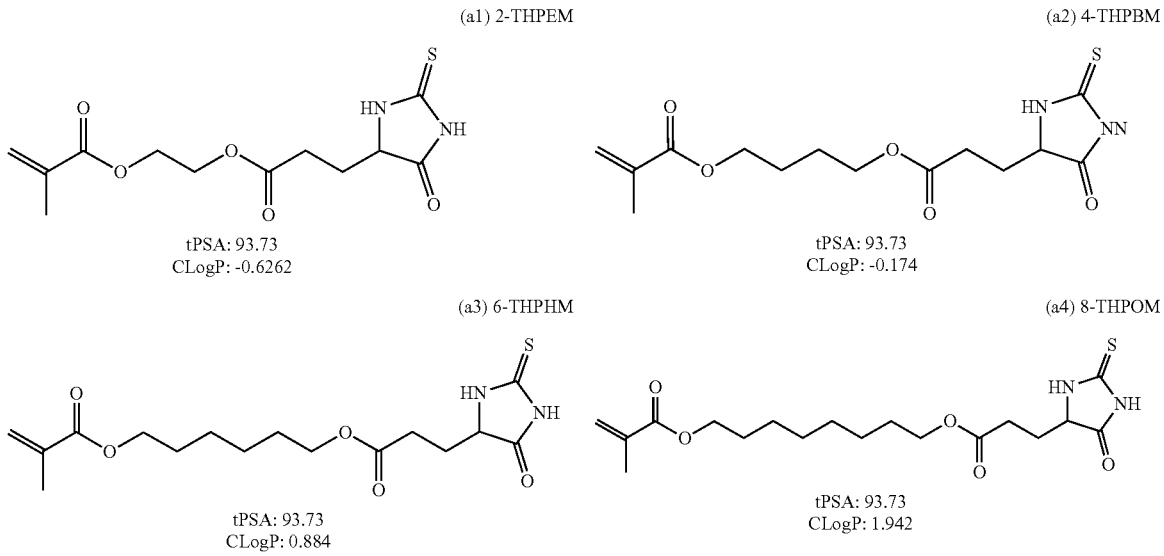

-continued
(a5) 10-THPDM
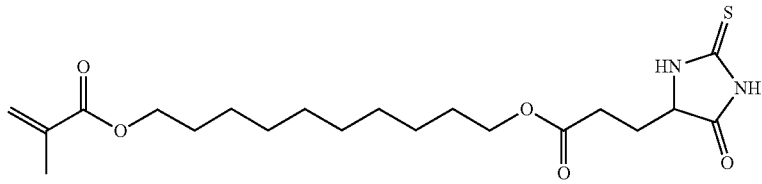
tPSA: 93.73
CLogP: 3
(a6) 12-THPDDM
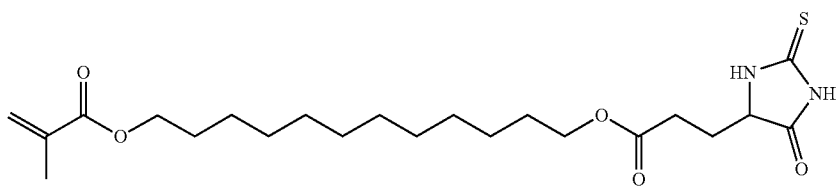
tPSA: 93.73
CLog: 4.058
[Chem. 9]
(a7)
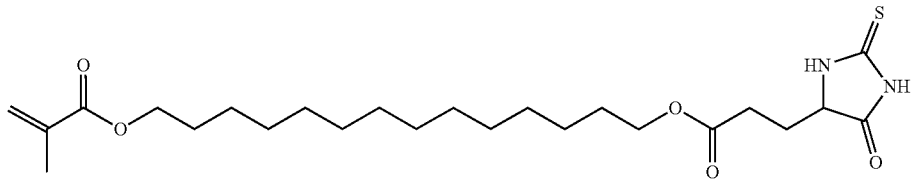
14-THPTDM
tPSA: 93.73
CLogP: 5.116
(a8)
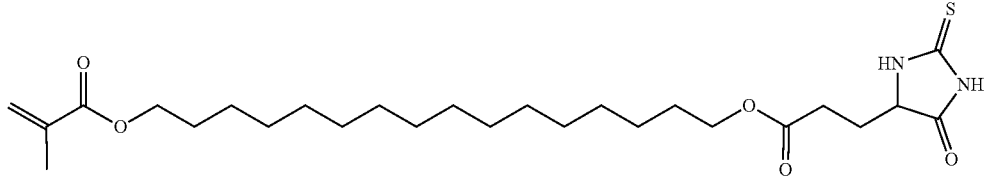
16-THPHDM
tPSA: 93.73
CLogP: 6.174
(a9)
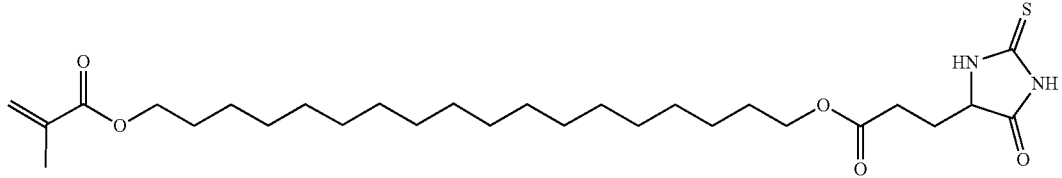
tPSA: 93.73
CLogP: 7.232

-continued
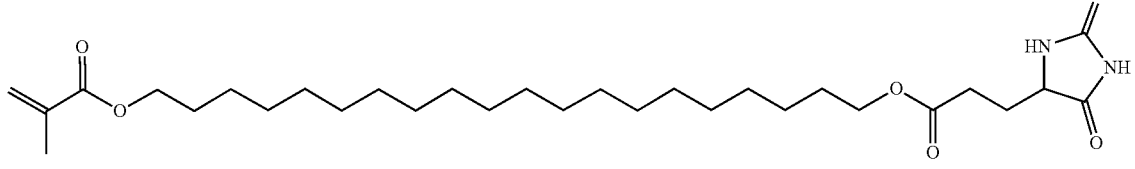
(a10)
tPSA: 93.73
CLogP: 8.29
[Chem. 10]
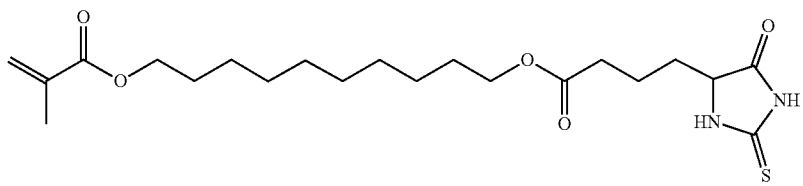
(a11)
tPSA: 93.73
CLogP: 3.529
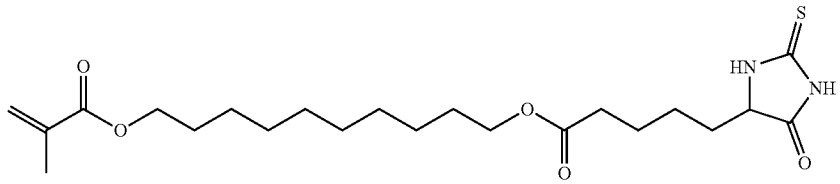
(a12)
tPSA: 93.73
CLogP: 4.058
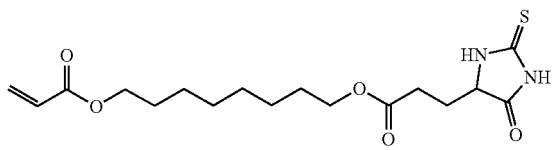
(a13)
tPSA: 93.73
CLogP: 1.633
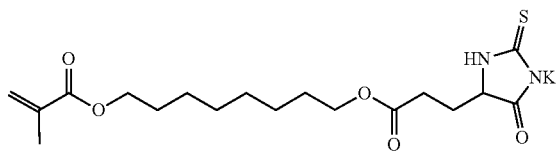
(a14)
tPSA: 84.94
CLogP: 1.949
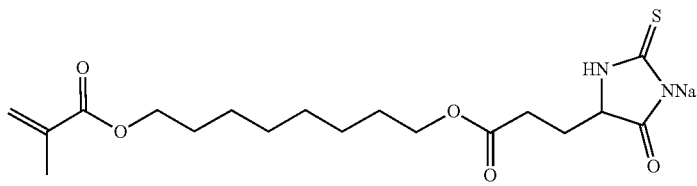
(a15)
tPSA: 84.94
CLogP: 1.949

(a16)
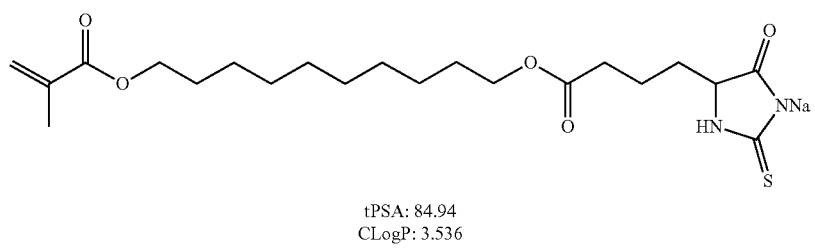
tPSA: 84.94
CLogP: 3.536
Specific examples of the compounds (A) further include the following compounds.
[Chem. 11]
(a17)
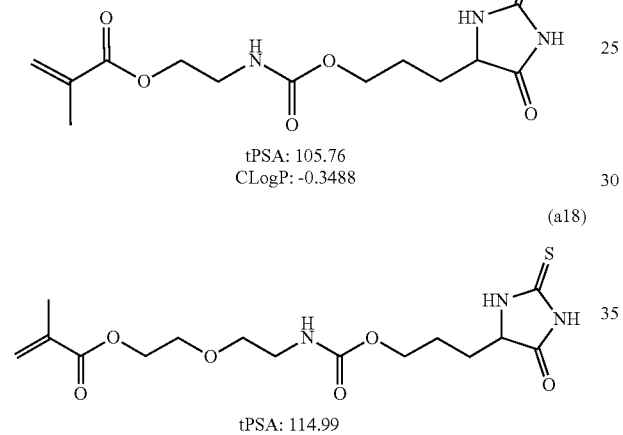
tPSA: 105.76
CLogP: −0.3488
(a18)
tPSA: 114.99
CLogP: −0.2844
(a19)
tPSA: 67.43
CLogP: −0.191
(a20)
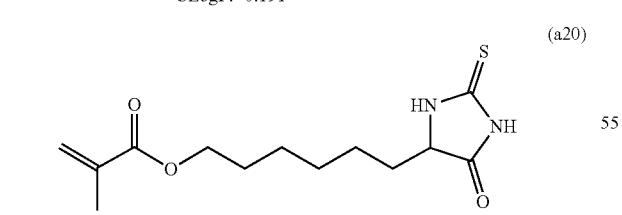
tPSA: 67.43
CLogP: 1.396
(a21)
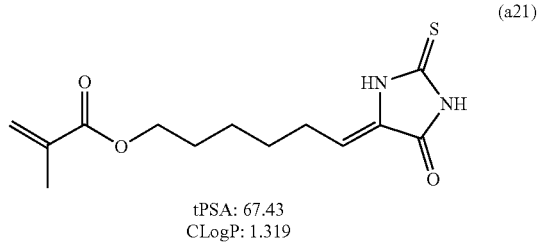
tPSA: 67.43
CLogP: 1.319
(a22)
tPSA: 67.43
CLogP: 2.454
(a23)
tPSA: 67.43
CLogP: 2.377
(a24)
tPSA: 67.43
CLogP: 3.512
(a25)
tPSA: 67.43
CLogP: 3.435

[Chem. 12]

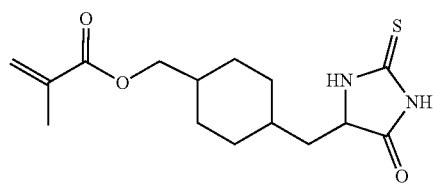
(a26)
tPSA: 67.43
CLogP: 1.92

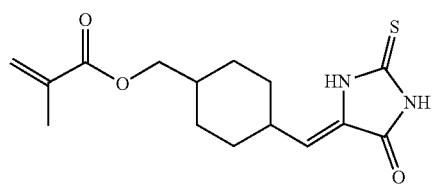
(a27)
tPSA: 67.43
CLogP: 1.843

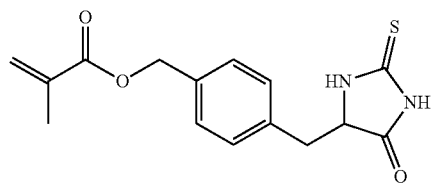
(a28)
tPSA: 67.43
CLogP: 1.018

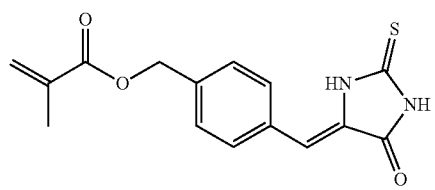
(a29)
tPSA: 67.43
CLogP: 1.321

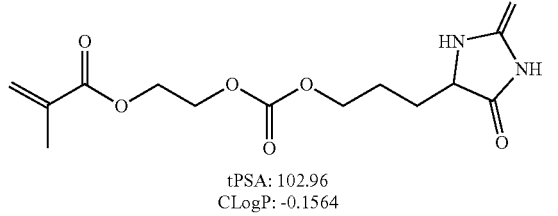
(a30)
tPSA: 102.96
CLogP: -0.1564

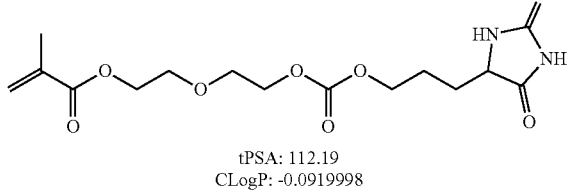
(a31)
tPSA: 112.19
CLogP: -0.0919998

Of the compounds illustrated above, (a5), (a24) and (a25) are preferable from the point of view of solubility.

For example, the compounds (A) may be produced by the following method.

For example, the compounds (a1) to (a10) and (a13) to (a15), which are examples of the compounds (A), are condensates of 2-thiohydantoin-5-propionic acid and hydroxyalkyl (meth)acrylate, and may be produced by a known condensation reaction.

The compounds (a11) and (a16) are condensates of 2-thiohydantoin-5-butanoic acid and hydroxyalkyl (meth)acrylate, and may be produced by a known condensation reaction.

The compound (a12) is a condensate of 2-thiohydantoin-5-pentanoic acid and hydroxyalkyl (meth)acrylate, and may be produced by a known condensation reaction.

The compounds (a17) and (a18) may be produced by reducing the carboxyl group of 2-thiohydantoin-5-propionic acid to a hydroxyl group and then reacting it with an isocyanate compound having a methacryloyl group to form a carbamate.

The compounds (a19) to (a29), which are examples of the compounds (A), may be produced by condensing methacrylic acid with a hydroxyl group at the end of a substituent extending from the 5-position of 2-thiohydantoin.

The compounds (a30) and (a31), which are examples of the compounds (A), may be produced by reacting a hydroxyl group at the end of a substituent extending from the 5-position of 2-thiohydantoin, with a chlorocarbonate ester derivative.

By the above condensation reactions, the compounds (A) may be preferably obtained with a purity of not less than 50 mass %, more preferably not less than 70 mass %, and still more preferably not less than 85 mass %. When the purity of the compound (A) is 50 mass % or above, an adhesive composition of the present invention advantageously exhibits stable adhesion, and also stably effectively enhances the adhesion, with respect to noble metals and alloys thereof. The purity of the compound (A) may be measured using $^1$H-NMR, FT-IR or HPLC.

The compounds (A) are compounds having excellent solubility with respect to solvents and are suited for bonding applications. For example, the compound (A) is a sulfur-containing polymerizable monomer that shows adhesion or effectively enhances the adhesion with respect to noble metals and noble metal alloys, can be mixed at a high concentration with an organic solvent and/or a radically polymerizable monomer, and does not adversely affect the adhesion with respect to the surface of the tooth substances or the surface of zirconium oxide or the like.

[Adhesive Compositions]

An adhesive composition of the present invention (hereinafter, also written simply as the "composition of the present invention") contains the compound (A) of the present invention. The composition of the present invention shows high adhesion, and also effectively enhances the adhesion, with respect to metals, in particular, noble metals such as gold, silver, platinum and palladium, or alloys containing noble metals (hereinafter, also written as the "noble metal alloys"). Here, the phrase "effectively enhances the adhesion" means that the composition of the present invention used as a primer described below effectively enhances the adhesion of an adhesive material that is used.

The composition of the present invention is suitably used in medical or dental applications. The composition of the present invention is useful as an adhesive material, a primer, a bone cement, a bonding material, a sealant, a cement, a filling material, a backing material, an abutment, a mobile tooth fixing material, or a root canal filling material each used in medical or dental applications. Of these, the composition of the present invention is useful as an adhesive material for bonding an adherend such as a tooth substance together with a noble metal or a noble metal alloy, an adhesive material for bonding noble metals or noble metal alloys together, or a primer (a pretreatment material) applied to the bonding surface of a noble metal or a noble metal alloy to enhance the adhesion between the noble metal or the noble metal alloy and an adherend such as a tooth substance, or to enhance the adhesion between the noble metal or the noble metal alloy and another noble metal or noble metal alloy.

The composition of the present invention contains the compound (A). The compound (A) has little adverse effects, for example, does not cause a significant decrease in the bond strength with respect to the surface of a tooth substance or the surface of a ceramic such as zirconium oxide. Further, the compound (A) may be added to a conventional adhesive material without causing a significant adverse effect on the bond strength of the adhesive material with respect to the surface of the tooth substances or the surface of ceramics.

Some example of adhesion targets made of noble metals or noble metal alloys are prostheses such as inlays, onlays, crowns, bridges and dentures.

The composition of the present invention is a versatile adhesive composition that can be satisfactorily used as an adhesive material in all fields including the precision machinery and jewelry industries where, for example, organic materials and noble metals or noble metal alloys are bonded. Specifically, the composition of the present invention may be used as a general industrial adhesive material, an artistic handcraft adhesive material or a jewelry adhesive material, and may be also used by being added to a paint, a gap filling material, a construction adhesive material, a covering material, etc.

The composition of the present invention may be a one-liquid type or a one-paste type, or may be a multi-pack type such as a two-liquid type, a powder/liquid type or a paste & paste type. In the case of a multi-pack type, for example, the components stored separately in the form of multiple packs may be mixed together immediately before use.

The composition of the present invention may further include at least one component selected from radically polymerizable monomers (B) other than the compounds (A), silane coupling agents (C), fillers (D), polymerization initiators (E), reducing compounds (F), organic solvents (G) and waters (H).

《Compounds (A)》

The lower limit of the proportion of the compound (A) in 100 mass % of the composition of the present invention is preferably 0.01 mass %, more preferably 0.05 mass %, and still more preferably 0.1 mass %, and the upper limit of the proportion is preferably 30 mass %, more preferably 10 mass %, and still more preferably 5.0 mass %. This configuration ensures that the composition of the present invention will show high adhesion and effectively enhance the adhesion with respect to noble metals and noble metal alloys, and will also have excellent polymerizability.

《Radically polymerizable monomers (B)》

The composition of the present invention may contain a radically polymerizable monomer (B) other than the compounds (A). The radically polymerizable monomers (B) exclude components that correspond to the silane coupling agents (C) described later.

Examples of the radically polymerizable monomers (B) include radically polymerizable monomers (B1) free from acidic groups and salts thereof (hereinafter, also written as the "components (B1)"), and radically polymerizable monomers (B2) having at least one selected from acidic groups and salts thereof (hereinafter, also written as the "components (B2)").

《《Components (B1)》》

Examples of the components (B1) include monofunctional radically polymerizable monomers free from acidic groups and salts thereof, and polyfunctional radically polymerizable monomers free from acidic groups and salts thereof.

In the present specification, the term "monofunctional" in the monofunctional radically polymerizable monomers means that the monomers have one ethylenically unsaturated group, and the term "polyfunctional" in the polyfunctional radically polymerizable monomers means that the monomers have two or more ethylenically unsaturated groups.

Examples of the monofunctional radically polymerizable monomers include:

monofunctional (meth)acrylates, specifically, alkyl (meth)acrylates such as methyl (meth)acrylate, ethyl (meth)acrylate, propyl (meth)acrylate, butyl (meth)acrylate, pentyl (meth)acrylate and hexyl (meth)acrylate; aromatic ring-containing (meth)acrylates such as phenyl (meth)acrylate and 2-hydroxy-3-phenoxypropyl (meth)acrylate; isocyanate group-containing (meth)acrylates such as (meth)acryloyloxyethyl isocyanate; and amino group-containing (meth)acrylates such as N,N-dimethylaminoethyl (meth)acrylate and N,N-diethylaminoethyl (meth)acrylate; and other monofunctional radically polymerizable monomers, specifically, aromatic vinyl compounds such as styrene; aliphatic vinyl compounds such as (meth)acrylonitrile; and vinyl esters such as vinyl acetate.

Examples of the polyfunctional radically polymerizable monomers include:

polyfunctional (meth)acrylates, specifically, alkanepolyol poly(meth)acrylates such as ethylene glycol di(meth)acrylate, propylene glycol di(meth)acrylate, 1,6-hexanediol di(meth)acrylate, neopentyl glycol di(meth)acrylate, glycerol di(meth)acrylate and trimethylolpropane tri(meth)acrylate; polyethylene glycol di(meth)acrylates (number of ethylene glycol chains: n=less than 6) such as diethylene glycol di(meth)acrylate and triethylene glycol di(meth)acrylate; polypropylene glycol di(meth)acrylates (number of propylene glycol chains: n=12 or less) such as dipropylene glycol di(meth)acrylate, tripropylene glycol di(meth)acrylate and nonapropylene glycol di(meth)acrylate; aromatic ring-containing polyfunctional (meth)acrylates (excluding those corresponding to the following urethane (meth)acrylates); and urethane (meth)acrylates; and other polyfunctional radically polymerizable monomers, specifically, aromatic vinyl compounds such as divinylbenzene.

Examples of the aromatic ring-containing polyfunctional (meth)acrylates include addition reaction products formed between 1 mol of bisphenol A and 2 mol of glycidyl (meth)acrylate (Bis-GMA in the case of glycidyl methacrylate), condensates formed between 1 mol of bisphenol A epichlorohydrin condensate and 2 mol of (meth)acrylic acid, and condensates formed between 1 mol of bisphenol A ethylene oxide adduct and 2 mol of (meth)acrylic acid (number of ethylene oxide chains added: m+n≥2 where m and n are each the number of ethylene oxide chains added to the phenolic hydroxyl group on one side of the bisphenol A).

Examples of the urethane (meth)acrylates include addition reaction products formed between 2 mol of a hydroxyl group-containing (meth)acrylate and 1 mol of a diisocyanate. Examples of the hydroxyl group-containing (meth) acrylates include hydroxyalkyl (meth)acrylates such as 2-hydroxyethyl (meth)acrylate, 3-hydroxypropyl (meth) acrylate, 4-hydroxybutyl (meth)acrylate, 6-hydroxyhexyl (meth)acrylate and 10-hydroxydecyl (meth)acrylate. Examples of the diisocyanates include aliphatic diisocyanates such as hexamethylene diisocyanate and trimethylhexamethylene diisocyanate; alicyclic diisocyanates such as isophorone diisocyanate; and aromatic diisocyanates such as tolylene diisocyanate, xylylene diisocyanate and diphenylmethane diisocyanate.

Specific examples of the urethane (meth)acrylates include 2,2,4-trimethylhexamethylene bis (2-carbamoyloxyethyl) di(meth)acrylate (UDMA in the case of methacrylate).

⟨ ⟨ Components (B2) ⟩ ⟩

The components (B2) have at least one selected from acidic groups and salts thereof. Examples of the acidic groups in the present specification include carboxyl groups, acid anhydride groups, phosphoric acid groups, thiophosphoric acid groups and sulfonic acid groups. The acidic groups may be partially or completely in the form of a salt such as a monovalent or polyvalent metal salt or ammonium salt. In this case, it is usually preferable that the component (B2) having a salt of an acidic group come to act as an acid when the component (B2) having a salt of an acidic group is used together with and contacted with other acidic compound.

Examples of the monofunctional radically polymerizable monomers having a carboxyl group or an anhydride group thereof include monocarboxylic acids, dicarboxylic acids, tricarboxylic acids, tetracarboxylic acids and polycarboxylic acids, and acid anhydrides thereof. Specific examples include (meth)acrylic acid, p-vinylbenzoic acid, 2-, 3- or 4-(meth)acryloyloxybenzoic acid, 6-(meth)acryloyloxyhexamethylenemalonic acid, 10-(meth)acryloyloxydecamethylenemalonic acid, maleic acid, 4-(meth)acryloyloxymethyltrimellitic acid and the anhydride thereof, 4-(meth) acryloyloxyethyltrimellitic acid and the anhydride thereof, 4-(meth)acryloyloxybutyltrimellitic acid and the anhydride thereof, 4-[2-hydroxy-3-(meth)acryloyloxy]butyltrimellitic acid and the anhydride thereof, 11-(meth)acryloyloxy-1,1-undecanedicarboxylic acid, 2,3-bis (3,4-dicarboxybenzoyloxy)propyl (meth)acrylate, 6-(meth)acryloyloxyethylnaphthalene-1,2,6-tricarboxylic acid, O-(meth)acryloyloxytyrosine, N-(meth)acryloyloxytyrosine, N-(meth)acryloyloxyphenylalanine, N-(meth)acryloyl p-aminobenzoic acid, N-(meth)acryloyl o-aminobenzoic acid, adducts of N-phenylglycine or N-tolylglycine with glycidyl (meth)acrylate, 4-[(2-hydroxy-3-(meth)acryloyloxypropyl)amino]phthalic acid, 3- or 4-[N-methyl-N-(2-hydroxy-3-(meth))acryloyloxypropyl)amino]phthalic acid, (meth)acryloylaminosalicylic acid and (meth)acryloyloxysalicylic acid.

Of the above monomers, 11-methacryloyloxy-1,1-undecanedicarboxylic acid (MAC-10), and 4-methacryloyloxyethyltrimellitic acid (4-MET) and the anhydride thereof (4-META) are preferable.

Examples of the polyfunctional radically polymerizable monomers having a carboxyl group or an anhydride group thereof include monocarboxylic acids, dicarboxylic acids, tricarboxylic acids and tetracarboxylic acids, and acid anhydrides thereof. Specific examples include N,O-di(meth)acryloyloxytyrosine, addition reaction products formed between 2 mol of 2-hydroxyethyl (meth)acrylate and 1 mol of pyromellitic dianhydride, addition reaction products formed between 2 mol of 2-hydroxyethyl (meth)acrylate and 1 mol of 3,3',4,4'-benzophenonetetracarboxylic dianhydride or 3,3',4,4'-biphenyltetracarboxylic dianhydride, and 2-(3,4-dicarboxybenzoyloxy)-1,3-di(meth)acryloyloxypropane.

Examples of the radically polymerizable monomers having a phosphoric acid group include 2-(meth)acryloyloxyethyl acid phosphate, 2- or 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis{2-(meth)acryloyloxyethyl} acid phosphate, bis{2- or 3-(meth)acryloyloxypropyl} acid phosphate, 2-(meth)acryloyloxyethylphenyl acid phosphate and 2-(meth)acryloyloxyethyl p-methoxyphenyl acid phosphate.

Of the above monomers, 2-(meth)acryloyloxyethylphenyl acid phosphate and 10-(meth)acryloyloxydecyl acid phosphate are preferable.

In the above specific examples of the radically polymerizable monomers having a phosphoric acid group, the phosphoric acid group may be replaced by a thiophosphoric acid group. Examples of such radically polymerizable monomers having a thiophosphoric acid group include those monomers described in JP-A-S54-21438, JP-A-S59-140276 and JP-A-S59-142268. More specifically, the monomers may be exemplified by the following compounds and tautomers shown in the brackets [ ].

[Chem. 13]

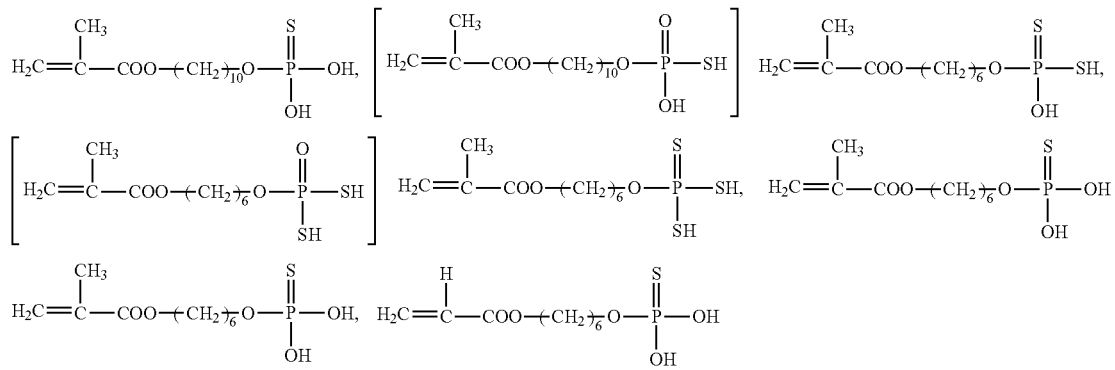

-continued

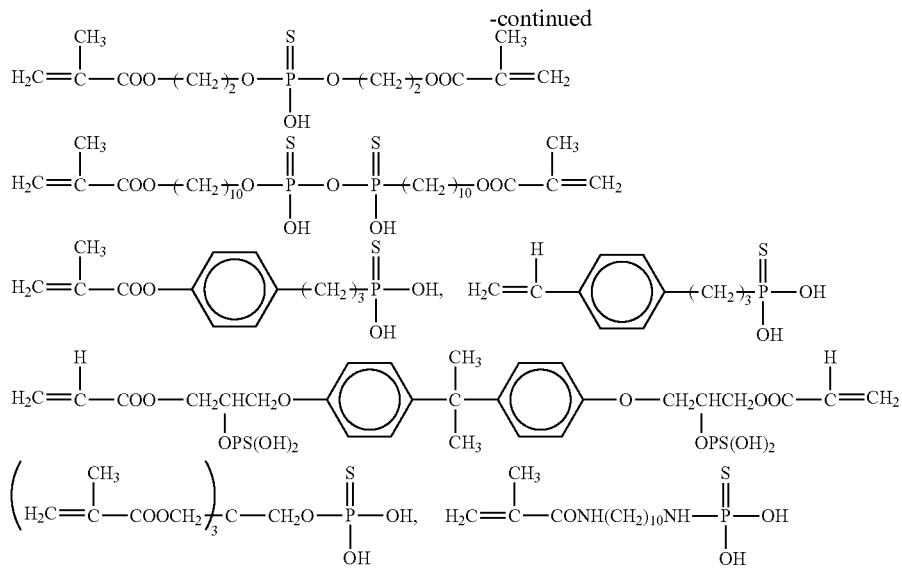

Examples of the radically polymerizable monomers having a sulfonic acid group include 2-sulfoethyl (meth)acrylate, 2- or 1-sulfo-1- or 2-propyl (meth)acrylate, 1- or 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl(meth)acrylamide and 2-methyl-2-(meth)acrylamidopropanesulfonic acid. Of these, 2-methyl-2-(meth)acrylamidopropanesulfonic acid is preferable.

The relative contents of the compound (A) and the radically polymerizable monomer (B) in the composition of the present invention may be changed appropriately in accordance with the purpose of use of the composition of the present invention. In 100 mass % of the total of the compound (A) and the radically polymerizable monomer (B), the lower limit of the proportion of the compound (A) is preferably 0.01 mass %, more preferably 0.05 mass %, and still more preferably 0.1 mass %, and the upper limit of the proportion is preferably 30 mass %, more preferably 20 mass %, still more preferably 10 mass %, and particularly preferably 5 mass %. This configuration ensures that the composition of the present invention will show high adhesion and effectively enhance the adhesion with respect to noble metals and noble metal alloys, and will also have excellent polymerizability.

⟨ Silane Coupling Agents (C) ⟩

The composition of the present invention may include a silane coupling agent (C).

Examples of the silane coupling agents (C) include silane coupling agents widely known in the industry, and polymerizable monomers having an alkoxysilyl group. Examples of the polymerizable monomers having an alkoxysilyl group include (meth)acryloyloxyalkyltrimethoxysilanes such as γ-(meth)acryloyloxypropyltrimethoxysilane, vinyltriethoxysilane, vinyl-tris(2-methoxyethoxy)silane, allyltriethoxysilane, 2-styrylethyltrimethoxysilane, (meth)acryloyloxyethyldimethyl(3-trimethoxysilylpropyl)ammonium chloride, 3-(N-styrylmethyl-2-aminoethylamino)propyltrimethoxysilane hydrochloride and trimethoxysilylpropylallylamine. Of these, γ-(meth)acryloyloxypropyltrimethoxysilane and 2-styrylethyltrimethoxysilane are preferably used.

When the silane coupling agent (C) is used, the lower limit of the proportion of the silane coupling agent (C) in 100 mass % of the composition of the present invention is preferably 0.01 mass %, more preferably 0.05 mass %, and still more preferably 0.1 mass %, and the upper limit of the proportion is preferably 30 mass %, more preferably 20 mass %, and still more preferably 10 mass %.

⟨ Fillers (D) ⟩

The composition of the present invention may include a filler (D). Examples of the fillers (D) include organic fillers, inorganic fillers and organic composite fillers.

Examples of the organic fillers include fillers that are crushed powders of polymers obtained by polymerizing a polymerizable monomer, fillers that are crushed powders of polymers obtained by polymerizing a polymerizable monomer together with a crosslinking agent, and fillers that are powdery polymers obtained by the dispersion polymerization of a polymerizable monomer. Examples of the polymerizable monomers used as ingredients of the fillers include those polymerizable monomers described with respect to the radically polymerizable monomers (B).

For example, the polymer that forms an organic filler is a homopolymer obtained from a single polymerizable monomer, a copolymer obtained using a combination of polymerizable monomers, or a crosslinked polymer obtained using a polymerizable monomer together with a crosslinking agent. A polyfunctional polymerizable monomer capable of acting as a crosslinking agent may be used as at least part of the polymerizable monomer(s).

Specific examples of the polymers that form organic fillers include polymethyl methacrylate (PMMA), polyethyl methacrylate, polypropyl methacrylate, polybutyl methacrylate (PBMA) and polyvinyl acetate (PVAc).

Further, the organic fillers may be fillers that are crushed powders of polymers such as polyethylene glycol (PEG), polypropylene glycol (PPG) and polyvinyl alcohol (PVA).

Examples of the inorganic fillers include alkali glass, silica, silica alumina, alumina, alumina quartz; glasses including barium glass and strontium glass; zirconia, zirconium phosphate, calcium carbonate, kaolin, clay, mica, aluminum sulfate, barium sulfate, calcium sulfate, titanium oxide, calcium phosphate and hydroxyapatite.

Examples of the organic composite fillers include powders obtained by coating the surface of the above inorganic fillers with a polymer of a polymerizable monomer followed by crushing; and powders obtained by adding sol-gel particles to a polymerizable monomer, polymerizing and curing the mixture, and crushing the resultant polymer.

Specific examples of the organic composite fillers include fillers obtained by polymerizing polymerizable monomers having trimethylolpropane tri(meth)acrylate (TMPT) as main ingredient so as to coat the inorganic filler described above such as silica or zirconia, and crushing the resultant polymer (TMPT·f). The fillers may be treated beforehand with silane coupling agents widely known in the industry.

When the filler (D) is used, the lower limit of the proportion of the filler (D) in 100 mass % of the composition of the present invention is preferably 1 mass %, more preferably 5 mass %, and still more preferably 10 mass %, and the upper limit of the proportion is preferably 90 mass %, more preferably 80 mass %, and still more preferably 70 mass %. In an embodiment, the upper limit of the proportion is 60 mass %, 55 mass %, or 50 mass %.

⟨ Polymerization Initiators (E) ⟩

The composition of the present invention may include a polymerization initiator (E).

The polymerization initiator (E) may be used to initiate the polymerization of components such as the radically polymerizable monomer (B). Examples of the polymerization initiators (E) include photopolymerization initiators, peroxides and barbituric acid compounds.

The photopolymerization initiator has a role of curing the composition of the present invention by being optically excited by itself or in the presence of another compound. Examples of the photopolymerization initiators include α-ketocarbonyl compounds and acylphosphine oxide compounds.

Examples of the α-ketocarbonyl compounds include α-diketones, α-ketoaldehydes, α-ketocarboxylic acids and α-ketocarboxylic acid esters. More specific examples include α-diketones such as diacetyl, 2,3-pentadione, 2,3-hexadione, benzil, 4,4'-dimethoxybenzil, 4,4'-diethoxybenzil, 4,4'-oxybenzil, 4,4'-dichlorobenzil, 4-nitrobenzil, α-naphthyl, β-naphthyl, camphorquinone, camphorquinonesulfonic acid, camphorquinonecarboxylic acid and 1,2-cyclohexanedione; α-ketoaldehydes such as methylglyoxal and phenylglyoxal; pyruvic acid, benzoylformic acid, phenylpyruvic acid, methyl pyruvate, ethyl benzoylformate, methyl phenylpyruvate and butyl phenylpyruvate. Of these, α-diketones are preferable from points of view such as stability, and diacetyl, benzil and camphorquinone are preferable.

Examples of the acylphosphine oxide compounds include benzoyldimethoxyphosphine oxide, benzoylethoxyphenylphosphine oxide, benzoyldiphenylphosphine oxide, 2-methylbenzoyldiphenylphosphine oxide, diphenyl(2,4,6-trimethylbenzoyl)phosphine oxide and tributylphosphine. Of these, diphenyl(2,4,6-trimethylbenzoyl)phosphine oxide is preferable.

Examples of the peroxides include organic peroxides such as diacetyl peroxide, dipropyl peroxide, dibutyl peroxide, dicapryl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide and p,p'-dinitrodibenzoyl peroxide; and inorganic peroxides such as ammonium persulfate, potassium persulfate, potassium chlorate, potassium bromate and potassium superphosphate. Of these, BPO is preferable.

Examples of the barbituric acid compounds include 1,3,5-trimethylbarbituric acid, 1,3,5-triethylbarbituric acid, 1,3-dimethyl-5-ethylbarbituric acid, 1,5-dimethylbarbituric acid, 1-methyl-5-ethylbarbituric acid, 1-methyl-5-propylbarbituric acid, 5-ethylbarbituric acid, 5-propylbarbituric acid, 5-butylbarbituric acid, 5-methyl-1-butylbarbituric acid, 1-benzyl-5-phenylbarbituric acid, 1-cyclohexyl-5-ethylbarbituric acid, and alkali metal salts thereof. Thiobarbituric acid compounds may also be used.

When the polymerization initiator (E) is used, the lower limit of the content of the polymerization initiator (E) in the composition of the present invention is preferably 0.01 part by mass, more preferably 0.1 part by mass, and still more preferably 1.0 part by mass with respect to 100 parts by mass of the total of the compound (A) and the radically polymerizable monomer (B), and the upper limit of the content is preferably 20 parts by mass, more preferably 10 parts by mass, and still more preferably 5.0 parts by mass.

⟨ Reducing Compounds (F) ⟩

The composition of the present invention may include a reducing compound (F). When the polymerization initiator (E) is used in the composition of the present invention, the combined use of a reducing compound (F) allows for efficient polymerization. Further, when the composition of the present invention is used as a primer, a reducing compound (F) may be added to the composition of the present invention to serve as a curing catalyst for an adhesive material.

Examples of the reducing compounds (F) include organic reducing compounds such as amine compounds and salts thereof, and organic sulfinic acids and salts thereof; and inorganic reducing compounds.

The amine compounds may be any of aliphatic amines, alicyclic amines and aromatic amines; and may be any of primary amines, secondary amines and tertiary amines. Of these, aromatic amines are preferable, and aromatic tertiary amines are more preferable.

Examples of the amine compounds include dialkylaminoalkyls and (meth)acrylates thereof such as N,N-dimethylaminoethyl (meth)acrylate and N,N-diethylaminoethyl (meth)acrylate; aliphatic alkylaminoacetylbenzenes and aliphatic alkylaminoacylbenzenes such as triethylaminoacetylbenzene; aromatic tertiary amines such as methylaniline, dimethyl-p-toluidine and N,N-di(2-hydroxyethyl)-p-toluidine; N-phenylglycine (NPG), N-tolylglycine (NTG) and N,N-(3-methacryloyloxy-2-hydroxypropyl)phenylglycine (NPG-GMA). The (meth)acrylates also function as the components (B1) described hereinabove.

Examples of the organic sulfinic acids include alkanesulfinic acids such as ethanesulfinic acid, propanesulfinic acid, hexanesulfinic acid, octanesulfinic acid, decanesulfinic acid and dodecanesulfinic acid; alicyclic sulfinic acids such as cyclohexanesulfinic acid and cyclooctanesulfinic acid; and aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid.

Examples of the salts of the organic sulfinic acids include alkali metal salts, alkaline earth metal salts, amine salts and ammonium compound salts. The use of aromatic sulfinic acid salts is advantageous in that the discoloration is small of the adhesive composition and cured products obtained therefrom by polymerization curing.

Examples of the alkali metal salts include lithium salts, sodium salts and potassium salts. Examples of the alkaline earth metal salts include magnesium salts, calcium salts, strontium salts and barium salts. Examples of the amine salts include salts of primary amines such as methylamine, ethylamine, propylamine, butylamine, cyclohexylamine, aniline, toluidine, phenylenediamine and xylylenediamine; salts of secondary amines such as dimethylamine, diethylamine, dipropylamine, dibutylamine, piperidine, N-methylaniline, N-ethylaniline, diphenylamine and N-methyltoluidine; and salts of tertiary amines such as trimethylamine, triethylamine, pyridine, N,N-dimethylaniline, N,N-di(β-hydroxyethyl)aniline, N,N-diethylamine, N,N-dimethyltoluidine, N,N-diethyltoluidine and N,N-(β-hydroxyethyl)toluidine. Examples of the ammonium compound salts include ammonium salts, tetramethylammonium salts, tetraethylammonium salts, tetrapropylammonium salts and trimethylbenzylammonium salts.

Examples of the organic sulfinic acid salts include lithium benzenesulfinate, sodium benzenesulfinate, potassium benzenesulfinate, magnesium benzenesulfinate, calcium benzenesulfinate, strontium benzenesulfinate, barium benzenesulfinate, butylamine benzenesulfinate salt, aniline benzenesulfinate salt, toluidine benzenesulfinate salt, phenylenediamine benzenesulfinate salt, diethylamine benzenesulfinate salt, diphenylamine benzenesulfinate salt, triethylamine benzenesulfinate salt, ammonium benzenesulfinate salt, tetramethylammonium benzenesulfinate, trimethylbenzylammonium benzenesulfinate; lithium o-toluenesulfinate, sodium o-toluenesulfinate, potassium o-toluenesulfinate, calcium o-toluenesulfinate, cyclohexylamine o-toluenesulfinate salt, aniline o-toluenesulfinate salt, ammonium o-toluenesulfinate salt, tetraethylammonium o-toluenesulfinate, lithium p-toluenesulfinate, sodium p-toluenesulfinate, potassium p-toluenesulfinate, calcium p-toluenesulfinate, barium p-toluenesulfinate, ethylamine p-toluenesulfinate salt, toluidine p-toluenesulfinate salt, N-methylaniline p-toluenesulfinate salt, pyridine p-toluenesulfinate salt, ammonium p-toluenesulfinate salt, tetramethylammonium p-toluenesulfinate, sodium β-naphthalenesulfinate, strontium β-naphthalenesulfinate, triethylamine β-naphthalenesulfinate salt, N-methyltoluidine β-naphthalenesulfinate salt, ammonium β-naphthalenesulfinate salt and trimethylbenzylammonium β-naphthalenesulfinate.

Examples of the inorganic reducing compounds include reducing inorganic compounds having at least one atom selected from sulfur atoms and nitrogen atoms.

Examples of the inorganic reducing compounds having a sulfur atom include sulfurous acid, bisulfurous acid, metasulfurous acid, metabisulfurous acid, pyrosulfurous acid, thiosulfuric acid, dithionous acid, hyposulfurous acid, hydrosulfurous acid, and salts thereof. Of these, sulfites are preferable. Some preferred sulfites are sodium sulfite, potassium sulfite, sodium hydrogen sulfite and potassium hydrogen sulfite. Examples of the inorganic reducing compounds having a nitrogen atom include nitrites such as sodium nitrite, potassium nitrite, calcium nitrite and ammonium nitrite.

When the reducing compound (F) is used, the content of the reducing compound (F) in the composition of the present invention is preferably not less than 10 parts by mass and not more than 3000 parts by mass with respect to 100 parts by mass of the polymerization initiator (E).

⟨ Organic solvents (G) ⟩

The composition of the present invention may include an organic solvent (G). Examples of the organic solvents (G) include alcohol solvents such as methanol, ethanol, isopropyl alcohol and 2-ethylbutanol; ketone solvents such as acetone, methyl ethyl ketone, diethyl ketone, 2-butanone and 3-pentanone; ether solvents such as diethyl ether, n-butyl ether, 1,4-dioxane and tetrahydrofuran; ester solvents such as ethyl acetate; hydrocarbon solvents such as hexane, octane, benzene, toluene, xylene and p-cymene; and halogenated hydrocarbon solvents such as methylene chloride, chloroform, 1,2-dichloroethane and 1,1,2,2-tetrachloroethane.

The relative contents of the compound (A) and the organic solvent (G) in the composition of the present invention may be changed appropriately in accordance with the purpose of use of the composition of the present invention. In 100 mass % of the total of the compound (A) and the organic solvent (G), the lower limit of the proportion of the compound (A) is preferably 0.01 mass %, more preferably 0.05 mass %, and still more preferably 0.1 mass %, and the upper limit of the proportion is preferably 30 mass %, more preferably 20 mass %, and still more preferably 10 mass %. This configuration ensures that the composition of the present invention will show high adhesion and effectively enhance the adhesion with respect to noble metals and noble metal alloys, and will also have excellent polymerizability.

⟨ Waters (H) ⟩

The composition of the present invention may include water (H). The water (H) is not particularly limited and may be, for example, tap water, sterilized water or redox water. In medical and dental applications, pure water, distilled water, ion-exchanged water and purified water (e.g., pharmacopeial purified water) may be preferably used.

When the water (H) is used, the lower limit of the proportion of the water (H) in 100 mass % of the composition of the present invention is preferably 1 mass %, more preferably 3 mass %, and still more preferably 5 mass %, and the upper limit of the proportion is preferably 80 mass %, more preferably 70 mass %, and still more preferably 60 mass %.

When the organic solvent (G) and/or the water (H) is used, the lower limit of the total proportion of the organic solvent (G) and the water (H) (including the case where the content of any one of the organic solvent (G) and the water (H) is 0) in 100 mass % of the composition of the present invention is preferably 5 mass %, more preferably 10 mass %, and still more preferably 20 mass %, and the upper limit of the proportion is preferably 99.5 mass %, more preferably 90 mass %, and still more preferably 85 mass %.

⟨ Other Components ⟩

The composition of the present invention may include other components such as modifiers, thickeners, dyes, pigments and polymerization inhibitors in appropriate amounts while still ensuring that the performance of the composition is not impaired.

The composition of the present invention may include a sulfur-containing compound such as 6-(4-vinylbenzyl-n-propyl)amino-1,3,5-triazine-2,4-dithione (VBATDT) [see JP-A-S64-83254], a monomer including thiophosphoric acid [see JP-A-H01-138282], or 6-[(2-thioxo-4-oxo-1,2,3,4-tetrahydropyrimidin)-5-ylcarbonyl]hexyl methacrylate (MTU-6: thiouracil derivative) [see JP-A-H10-1409]. These compounds are usually classified as the radically polymerizable monomers (B).

[Dental Primer Compositions]

Dental primer compositions, which are a particularly preferred use application of the compositions of the present invention, will be described in detail below. A dental primer composition of the present invention is suitably used in the pretreatment of various dental prostheses made of noble metals or noble metal alloys before the dental prosthesis is bonded to a tooth substance or to another dental prosthesis using a (meth)acrylate-based adhesive material.

The (meth)acrylate-based adhesive materials may be any known dental adhesive materials that are compositions containing a (meth)acrylate monomer as a main component and a polymerization initiator. Examples of the (meth)acrylate monomers include the (meth)acrylates described as the polymerizable monomers (B) in the compositions of the present invention. Examples of the polymerization initiators include photopolymerization initiators, thermal polymerization initiators and chemical polymerization initiators.

EXAMPLES

Hereinbelow, the present invention will be described in greater detail based on Examples. However, it should be construed that the scope of the present invention is not limited to such Examples. In the following description, "parts" means "parts by mass" unless otherwise mentioned.

[Production Example 1] [Synthesis of 2-((3-(5-oxo-2-thioxoimidazolidin-4-yl)propanoyl)oxy)ethyl methacrylate (Abbreviated as 2-THPEM)]

[Chem. 14]

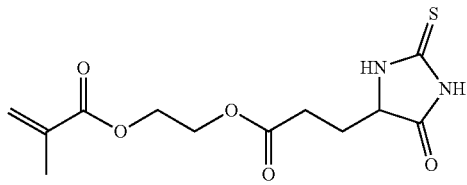

Under a nitrogen atmosphere, a 300 ml four-necked flask was loaded with 3.97 g (21.1 mmol) of 2-thiohydantoin-5-propionic acid, 3.1 ml (25.3 mmol) of 2-hydroxyethyl methacrylate, 4.0 mg of 2,6-di-tert-butyl-4-methylphenol and 0.51 g (4.22 mmol) of 4-dimethylaminopyridine. These were dissolved by the addition of 90 ml of tetrahydrofuran. A solution of 5.19 g (22.2 mmol) of dicyclohexylcarbodiimide in 30 ml of tetrahydrofuran was added dropwise to the flask at room temperature, and the mixture was stirred at room temperature for 3.0 hours. Thereafter, 150 ml of ethyl acetate and 30 ml of hexane were added to the reaction solution in the flask, and the mixture was stirred for 10 minutes. The mixture in the flask that was a white slurry was filtered through a pad of Celite, and the filtrate was concentrated under reduced pressure. The oil thus obtained was purified by silica gel chromatography (column: Biotage SNAP KP-Sil Cartridge 100 g; eluent solvent: ethyl acetate-hexane gradient, ethyl acetate 5%→100%). Thus, the title compound was obtained as a colorless oil weighing 3.12 g. (Yield: 49%)

$^1$H-NMR (270 MHz, CDCl$_3$) δ: 8.30 (1H, brd. s), 7.66 (1H, brd. s), 6.17-6.16 (1H, m), 5.64-5.61 (1H, m), 4.49-4.29 (5H, m), 2.58-2.52 (2H, m), 2.35-2.23 (1H, m), 2.11-1.98 (1H, m), 1.97 (3H, m).

[Production Example 2] [Synthesis of 4-((3-(5-oxo-2-thioxoimidazolidin-4-yl)propanoyl)oxy)butyl methacrylate (Abbreviated as 4-THPBM)]

[Chem. 15]

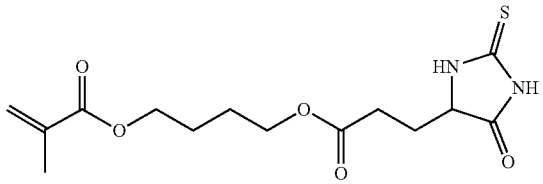

Under a nitrogen atmosphere, a 300 ml four-necked flask was loaded with 4.76 g (25.3 mmol) of 2-thiohydantoin-5-propionic acid, 4.809 g (30.4 mmol) of 4-hydroxybutyl methacrylate, 5.0 mg of 2,6-di-tert-butyl-4-methylphenol and 0.62 g (5.1 mmol) of 4-dimethylaminopyridine. These were dissolved by the addition of 90 ml of tetrahydrofuran. At room temperature, 5.49 g (26.6 mmol) of dicyclohexylcarbodiimide was added into the flask, and the mixture was stirred at room temperature for 6 hours. Thereafter, 25 ml of ethyl acetate and 5 ml of hexane were added to the reaction solution in the flask, and the mixture was stirred for 10 minutes. The mixture in the flask that was a white slurry was filtered through a pad of Celite, and the filtrate was concentrated under reduced pressure. The oil thus obtained was purified by silica gel chromatography (column: Biotage SNAP KP-Sil Cartridge 100 g; eluent solvent: ethyl acetate-hexane gradient, ethyl acetate 5%→100%). Thus, the title compound was obtained as a light yellow solid weighing 4.62 g. (Yield: 56%)

$^1$H-NMR (270 MHz, CDCl$_3$) δ: 9.21 (1H, brd. s), 8.06 (1H, brd. s), 6.12 (1H, brd. s), 5.59-5.55 (1H, m), 4.30 (1H, t, J=5.9 Hz), 4.22-4.16 (4H, m), 2.57-2.52 (2H, m), 2.34-2.03 (2H, m), 1.95 (3H, s), 1.81-1.65 (4H, m).

HRMS (ESI): Calcd. for C$_{14}$H$_{21}$N$_2$O$_5$S ([M+H]$^+$): 329.1171.
Found: 329.1174.
IR (ATR) cm$^{-1}$: 2955, 1713, 1685, 1521, 1160.

[Production Example 3] [Synthesis of 6-((3-(5-oxo-2-thioxoimidazolidin-4-yl)propanoyl)oxy)hexyl methacrylate (Abbreviated as 6-THPHM)]

[Chem. 16]

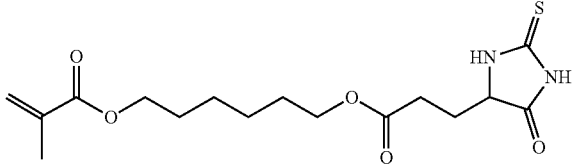

Under a nitrogen atmosphere, a 300 ml four-necked flask was loaded with 3.72 g (19.8 mmol) of 2-thiohydantoin-5-propionic acid, 3.69 g (19.8 mmol) of 6-hydroxyhexyl methacrylate, 5.0 mg of 2,6-di-tert-butyl-4-methylphenol and 0.48 g (3.9 mmol) of 4-dimethylaminopyridine. These were dissolved by the addition of 75 ml of tetrahydrofuran. At room temperature, 4.30 g (20.8 mmol) of dicyclohexylcarbodiimide was added into the flask and the mixture was stirred at room temperature for 6 hours. Thereafter, 25 ml of ethyl acetate and 5 ml of hexane were added to the reaction solution in the flask, and the mixture was stirred for 10 minutes. The mixture in the flask that was a white slurry was filtered through a pad of Celite, and the filtrate was concentrated under reduced pressure. The oil thus obtained was purified by silica gel chromatography (column: Biotage SNAP KP-Sil Cartridge 100 g; eluent solvent: ethyl acetate-hexane gradient, ethyl acetate 5%→100%). Thus, the title compound was obtained as a colorless oil weighing 2.38 g. (Yield: 34%)

$^1$H-NMR (270 MHz, DMSO-d6) δ: 11.70 (11.70 (1H, brd. s), 10.05 (1H, brd. s), 6.00 (1H, m), 5.65 (1H, q, J=1.3 Hz), 4.22 (1H, t, J=6.6 Hz), 4.07 (2H, t, J=6.6 Hz), 4.00 (2H, t, J=7.2 Hz), 2.41 (2H, t, J=7.6 Hz), 2.02-1.92 (1H, m), 1.86 (3H, d, J=1.3 Hz), 1.82-1.71 (1H, m), 1.62-1.54 (4H, m), 1.35-1.33 (4H, m).

HRMS (ESI): Calcd. for $C_{16}H_{25}N_2O_5S$ ([M+H]$^+$): 357.1484.

Found: 357.1490.

IR (ATR) cm$^{-1}$: 3238, 2934, 1714, 1636, 1517, 1161.

[Production Example 4] [Synthesis of 10-((3-(5-oxo-2-thioxoimidazolidin-4-yl)propanoyl)oxy)decyl methacrylate (Abbreviated as 10-THPDM)]

[Chem. 17]

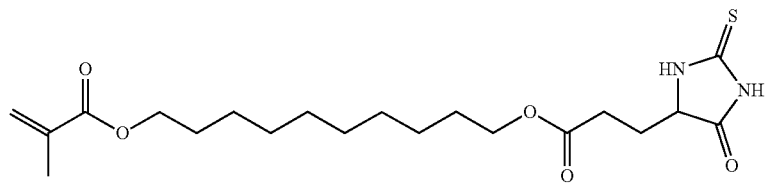

Under a nitrogen atmosphere, a 300 ml four-necked flask was loaded with 4.45 g (23.6 mmol) of 2-thiohydantoin-5-propionic acid, 6.88 g (28.4 mmol) of 10-hydroxydecyl methacrylate, 7.0 mg of 2,6-di-tert-butyl-4-methylphenol and 0.58 g (4.73 mmol) of 4-dimethylaminopyridine. These were dissolved by the addition of 90 ml of tetrahydrofuran. A solution of 5.82 g (24.8 mmol) of dicyclohexylcarbodiimide in 30 ml of tetrahydrofuran was added dropwise to the flask at room temperature, and the mixture was stirred at room temperature for 4.5 hours. Thereafter, 150 ml of ethyl acetate and 30 ml of hexane were added to the reaction solution in the flask, and the mixture was stirred for 10 minutes. The mixture in the flask that was a white slurry was filtered through a pad of Celite, and the filtrate was concentrated under reduced pressure. The oil thus obtained was purified twice by silica gel chromatography (column: Biotage SNAP KP-Sil Cartridge 100 g; eluent solvent: ethyl acetate-hexane gradient, ethyl acetate 5%→100%). Thus, the title compound was obtained as a colorless oil weighing 4.79 g. (Yield: 49%)

$^1$H-NMR (270 MHz, CDCl$_3$) δ: 8.45 (1H, brd. s), 7.53 (1H, brd. s), 6.10 (1H, m), 5.55 (1H, m), 4.26 (1H, dd, J=6.9, 4.9 Hz), 4.14 (2H, t, J=6.9 Hz), 4.10 (2H, t, J=6.9 Hz), 2.53 (2H, t, J=6.9 Hz), 2.34-2.21 (1H, m), 2.17-2.01 (1H, m), 1.95 (3H, m), 1.72-1.60 (4H, m), 1.43-1.26 (12H, m).

HRMS (ESI): Calcd. for $C_{20}H_{33}N_2O_5S$ ([M+H]$^+$): 413.2110.

Found: 413.2111.

IR (ATR) cm$^{-1}$: 3293, 2919, 2852, 1734, 1713, 1705, 1523, 1154.

[Production Example 5] [Synthesis of 3-(5-oxo-2-thioxoimidazolidin-4-yl)propyl methacrylate (a19)]

[Chem. 18]

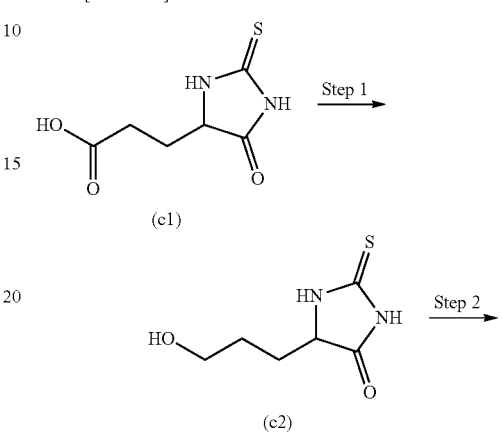

-continued

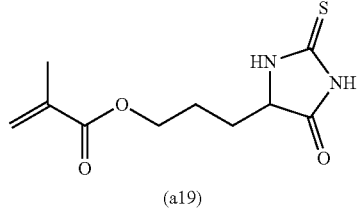

《Step 1》 [Synthesis of 5-(3-hydroxypropyl)-2-thioxoimidazolidin-4-one (c2)]

Under a nitrogen atmosphere, a 500 ml four-necked flask was loaded with 10.0 g (53.1 mmol) of 2-thiohydantoin-5-propionic acid, and 106 ml of tetrahydrofuran was added to give a solution. At 0° C., 64 ml (63.7 mmol) of borane-tetrahydrofuran complex (1.0 M tetrahydrofuran solution) was added dropwise to the flask, and the mixture was stirred at 0° C. for 1.5 hours and at room temperature for 17 hours. Thereafter, 200 ml of water was added to the reaction solution in the flask, and the mixture was stirred for 10 minutes. The mixture in the flask was concentrated under reduced pressure, and the residue was filtered through a pad of Celite. The filtrate was concentrated under reduced pressure. The oil thus obtained was purified by silica gel chromatography (column: Biotage Sfar D Cartridge 350 g; eluent solvent: ethyl acetate-hexane gradient, ethyl acetate 16%→100%). Thus, the title compound was obtained as a white solid weighing 5.19 g. (Yield: 56%)

$^1$H-NMR (270 MHz, DMSO-d$_6$) δ: 11.6 (1H, brd. s), 10.0 (1H, brd. s), 4.48 (1H, m), 4.20 (1H, t, J=5.6 Hz), 3.23-3.46 (2H, m) 1.36-1.82 (4H, m).

⟨ Step 2 ⟩ [Synthesis of 3-(5-oxo-2-thioxoimidazolidin-4-yl)propyl methacrylate (a19)]

Under a nitrogen atmosphere, a 500 ml four-necked flask was loaded with 4.00 g (23.0 mmol) of 5-(3-hydroxypropyl)-2-thioxoimidazolidin-4-one, 4.0 mg of 2,6-di-tert-butyl-4-methylphenol, 0.561 g (4.59 mmol) of 4-dimethylaminopyridine and 4.97 g (23.1 mmol) of dicyclohexylcarbodiimide. These were dissolved by the addition of 115 ml of tetrahydrofuran. At 0° C., 2.3 ml (27.6 mmol) of methacrylic acid was added dropwise to the flask, and the mixture was stirred at room temperature for 1 hour, at 50° C. for 4.5 hours and at room temperature for 15 hours. Thereafter, the reaction solution in the flask was filtered through a pad of Celite. Water was added to the filtrate, and the mixture was extracted with ethyl acetate (120 ml×3 times). The extracts were combined, dried over magnesium sulfate, and concentrated under reduced pressure. The oil thus obtained was purified by silica gel chromatography (column: Biotage Sfar D Cartridge 350 g; eluent solvent: ethyl acetate-hexane gradient, ethyl acetate 12%→62%). Thus, the title compound was obtained as a white solid weighing 1.79 g. (Yield: 32%)

$^1$H-NMR (270 MHz, DMSO-d$_6$) δ: 11.7 (1H, brd. s), 10.1 (1H, brd. s), 6.01 (1H, s), 5.67 (1H, s), 4.25 (1H, m), 4.00-4.15 (2H, m), 1.87 (3H, s), 1.54-1.83 (4H, m).

[Production Example 6] [Synthesis of 2-(((3-(5-oxo-2-thioxoimidazolidin-4-yl)propoxy)carbonyl)amino)ethyl methacrylate (a17)]

[Chem. 19]

(a17)

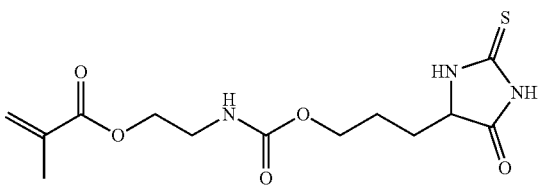

Under a nitrogen atmosphere, a 300 ml four-necked flask was loaded with 3.00 g (17.2 mmol) of 5-(3-hydroxypropyl)-2-thioxoimidazolidin-4-one, 3.0 mg of 2,6-di-tert-butyl-4-methylphenol and 0.10 ml (0.172 mmol) of dibutyltin dilaurate. These were dissolved by the addition of 55 ml of tetrahydrofuran. At 0° C., 2.7 ml (18.9 mmol) of 2-isocyanatoethyl methacrylate was added dropwise to the flask, and the mixture was stirred at room temperature for 1 hour. Thereafter, 1.1 ml (7.80 mmol) of 2-isocyanatoethyl methacrylate was added at 0° C. The mixture was stirred at room temperature for 2.5 hours. Thereafter, 200 ml of water was added to the reaction solution in the flask, and the mixture was stirred for 10 minutes. The mixture in the flask was extracted with ethyl acetate (90 ml×3 times). The extracts were combined, dried over magnesium sulfate, and concentrated under reduced pressure. The oil thus obtained was purified by silica gel chromatography (column: Biotage Sfar D Cartridge 100 g; eluent solvent: ethyl acetate-hexane gradient, ethyl acetate 16%→100%). Thus, the title compound was obtained as a white solid weighing 1.79 g. (Yield: 32%)

$^1$H-NMR (270 MHz, DMSO-d$_6$) δ: 11.7 (1H, brd. s), 10.0 (1H, brd. s), 7.29 (1H, brd. s), 6.04 (1H, s), 5.66 (1H, s), 4.21 (1H, m), 4.06 (2H, t, J=5.4 Hz), 3.85-4.01 (2H, m), 3.17-3.29 (2H, m), 1.86 (3H, s), 1.48-1.77 (4H, m).

[Production Example 7] [Synthesis of 2-(2-(((3-(5-oxo-2-thioxoimidazolidin-4-yl)propoxy)carbonyl)amino)ethoxy)ethyl methacrylate (a18)]

[Chem. 20]

(a18)

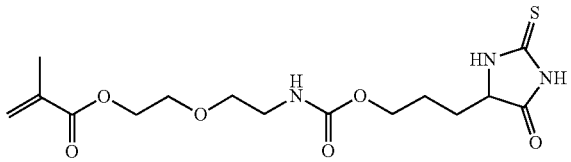

The procedures in the method described in Production Example 6 were repeated except that 2-isocyanatoethyl methacrylate used therein was replaced by 2-(2-isocyanatoethoxy)ethyl methacrylate. Thus, the title compound was obtained as a white solid weighing 157 mg. (Yield: 73%)

$^1$H-NMR (270 MHz, DMSO-d$_6$) δ: 11.7 (1H, brd. s), 10.1 (1H, brd. s), 7.11 (1H, brd. s), 6.02 (1H, s), 5.68 (1H, s), 4.12-4.38 (3H, m), 3.84-3.98 (2H, m), 3.55-3.74 (2H, m), 3.42 (2H, t, J=5.6 Hz), 3.03-3.19 (2H, m), 1.87 (3H, s), 1.47-1.80 (4H, m).

[Production Example 8] [Synthesis of 6-(5-oxo-2-thioxoimidazolidin-4-ylidene)hexyl methacrylate (a21)]

[Chem. 21]

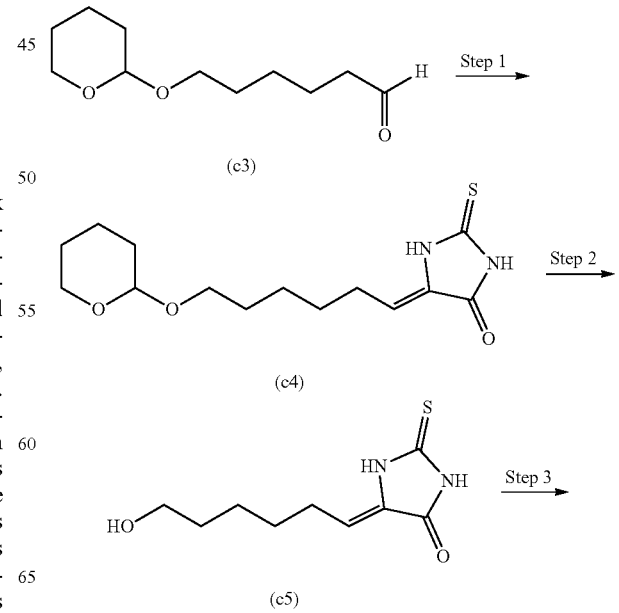

-continued

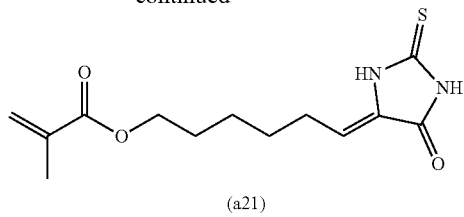

(a21)

⟨Step 1⟩ [Synthesis of 5-(6-((tetrahydro-2H-pyran-2-yl)oxy)hexylidene)-2-thioxoimidazolidin-4-one (c4)]

Under a nitrogen atmosphere, a 100 ml four-necked flask was loaded with 3.92 g (19.6 mmol) of 6-((tetrahydro-2H-pyran-2-yl)oxy)hexanal, 2.50 g (21.5 mmol) of 2-thiohydantoin, 4.8 ml (58.7 mmol) of pyridine and 0.97 ml (9.79 mmol) of piperidine. These were dissolved together. The mixture was stirred at room temperature for 2 hours. Thereafter, 30 ml of ethyl acetate and 30 ml of water were added to the reaction solution in the flask, and the mixture was stirred for 10 minutes. The mixture in the flask was extracted with ethyl acetate (30 ml×3 times). The extracts were combined and washed with 35 ml of 2 M hydrochloric acid. The extract was dried over magnesium sulfate and concentrated under reduced pressure. The oil thus obtained was purified by silica gel chromatography (column: Biotage Sfar D Cartridge 100 g; eluent solvent: ethyl acetate-hexane gradient, ethyl acetate 8%→47%). Thus, the title compound was obtained as a yellow oil weighing 4.85 g. (Yield: 83%)

$^1$H-NMR (270 MHz, CDCl$_3$) δ: 9.75 (2H, brd. s), 5.97 (1H, t, J=7.8 Hz), 4.64 (1H, s), 3.90 (1H, m), 3.76 (1H, m), 3.55 (1H, m), 3.44 (1H, m), 2.29 (2H, q, J=7.8 Hz), 1.37-1.91 (12H, m).

⟨Step 2⟩ [Synthesis of 5-(6-hydroxyhexylidene)-2-thioxoimidazolidin-4-one (c5)]

In an air atmosphere, a 300 ml recovery flask was loaded with 4.85 g (16.3 mmol) of 5-(6-((tetrahydro-2H-pyran-2-yl)oxy)hexylidene)-2-thioxoimidazolidin-4-one and 309 mg (0.721 mmol) of p-toluenesulfonic acid monohydrate. These were dissolved by the addition of 82 ml of methanol. The mixture was stirred at room temperature for 1 hour. Thereafter, the reaction solution in the flask was concentrated under reduced pressure. The oil thus obtained was purified by silica gel chromatography (column: Biotage Sfar D Cartridge 100 g; eluent solvent: ethyl acetate-hexane gradient, ethyl acetate 12%→100%). Thus, the title compound was obtained as a light yellow solid weighing 3.04 g. (Yield: 87%)

$^1$H-NMR (270 MHz, DMSO-d$_6$) δ: 12.0 (2H, brd. s), 5.64 (1H, t, J=7.9 Hz), 4.35 (1H, m), 3.23-3.44 (2H, m), 2.27 (2H, q, J=7.9 Hz), 1.20-1.50 (6H, m).

⟨Step 3⟩ [Synthesis of 6-(5-oxo-2-thioxoimidazolidin-4-ylidene)hexyl methacrylate (a21)]

Under a nitrogen atmosphere, a 300 ml four-necked flask was loaded with 4.73 g (22.1 mmol) of 5-(6-hydroxyhexylidene)-2-thioxoimidazolidin-4-one, 4.0 mg of 2,6-di-tert-butyl-4-methylphenol, 0.539 g (4.41 mmol) of 4-dimethylaminopyridine and 4.78 g (23.2 mmol) of dicyclohexylcarbodiimide. These were dissolved by the addition of 110 ml of tetrahydrofuran. At 0° C., 2.2 ml (26.5 mmol) of methacrylic acid was added dropwise to the flask. The mixture was stirred at room temperature for 3 hours and at 50° C. for 2 hours. Thereafter, the reaction solution in the flask was filtered through Celite. Water was added to the filtrate, and the mixture was extracted with ethyl acetate (110 ml×3 times). The extracts were combined, dried over magnesium sulfate, and concentrated under reduced pressure. The oil thus obtained was purified by silica gel chromatography (column: Biotage Sfar D Cartridge 200 g; eluent solvent: ethyl acetate-hexane gradient, ethyl acetate 8%→47%). Thus, the title compound was obtained as a light yellow solid weighing 3.46 g. (Yield: 55%)

$^1$H-NMR (270 MHz, DMSO-d$_6$) δ: 12.0 (2H, brd. s), 5.99 (1H, s), 5.64 (1H, s), 5.64 (1H, t, J=7.7 Hz), 4.07 (2H, t, J=6.4 Hz), 2.27 (2H, q, J=7.7 Hz), 1.85 (3H, s), 1.54-1.71 (2H, m), 1.24-1.50 (4H, m).

[Production Example 9] [Synthesis of 8-(5-oxo-2-thioxoimidazolidin-4-ylidene)octyl methacrylate (a23)]

[Chem. 22]

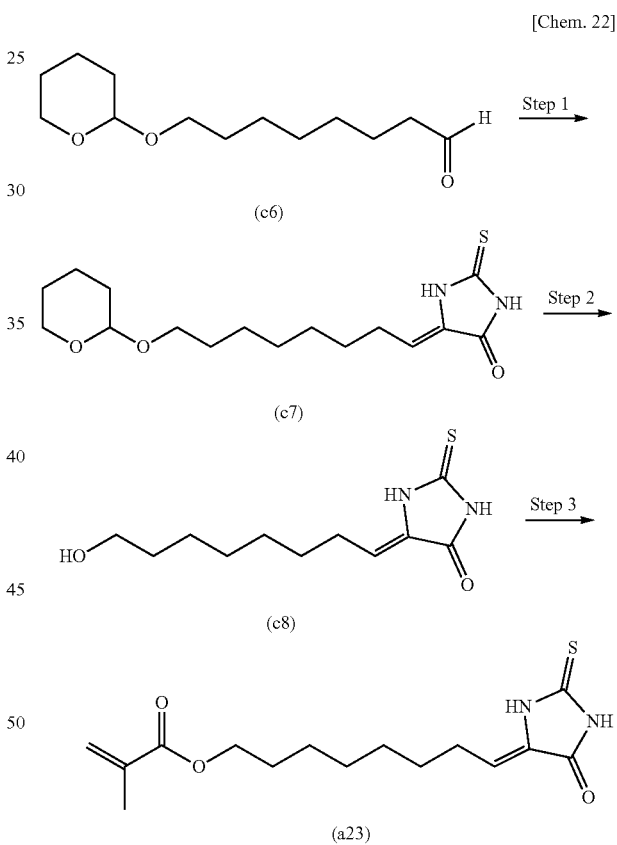

⟨Step 1⟩ [Synthesis of 5-(8-((tetrahydro-2H-pyran-2-yl)oxy)octylidene)-2-thioxoimidazolidin-4-one (c7)]

The procedures in Step 1 of the method described in Production Example 8 were repeated except that 6-((tetrahydro-2H-pyran-2-yl)oxy)hexanal (c3) used therein was replaced by 8-((tetrahydro-2H-pyran-2-yl)oxy)octanal (c6). Thus, the title compound was obtained as a white solid weighing 6.53 g. (Yield: 68%)

$^1$H-NMR (270 MHz, CDCl$_3$) δ: 9.74 (1H, brd. s), 9.42 (1H, brd. s), 5.95 (1H, t, J=7.9 Hz), 4.66 (1H, m), 4.14-3.73 (2H, m), 3.58-3.40 (2H, m), 2.30-2.22 (2H, m), 1.82-1.24 (16H, m).

⟨Step 2⟩ [Synthesis of 5-(8-hydroxyoctylidene)-2-thioxoimidazolidin-4-one (c8)]

The procedures in Step 2 of the method described in Production Example 8 were repeated except that 5-(8-((tetrahydro-2H-pyran-2-yl)oxy)octylidene)-2-thioxoimidazolidin-4-one (c7) obtained in Step 1 described above was used. Thus, the title compound was obtained as a white solid weighing 3.50 g. (Yield: 72%)

$^1$H-NMR (270 MHz, DMSO-d$_6$) δ: 12.0 (2H, brd. s), 5.64 (1H, t, J=7.8 Hz), 4.32 (1H, m), 3.17-3.53 (2H, m), 2.26 (2H, q, J=7.8 Hz), 1.14-1.52 (10H, m).

⟨Step 3⟩ [Synthesis of 8-(5-oxo-2-thioxoimidazolidin-4-ylidene)octyl methacrylate (a23)]

The procedures in Step 3 of the method described in Production Example 8 were repeated except that 5-(8-hydroxyoctylidene)-2-thioxoimidazolidin-4-one (c8) obtained in Step 2 described above was used. Thus, the title compound was obtained as a light yellow solid weighing 2.43 g. (Yield: 54%)

$^1$H-NMR (270 MHz, DMSO-d$_6$) δ: 12.0 (2H, brd. s), 5.99 (1H, s), 5.64 (1H, s), 5.64 (1H, t, J=7.7 Hz), 4.07 (2H, t, J=6.6 Hz), 2.26 (2H, q, J=7.7 Hz), 1.86 (3H, s), 1.48-1.69 (2H, m), 1.20-1.48 (8H, m).

[Production Example 10] [Synthesis of 10-(5-oxo-2-thioxoimidazolidin-4-ylidene)decyl methacrylate (a25)]

⟨Step 1⟩ [Synthesis of 5-(10-((tetrahydro-2H-pyran-2-yl)oxy)decylidene)-2-thioxoimidazolidin-4-one (c10)]

Procedures in accordance with Step 1 of the method described in Production Example 8 were conducted using 10-((tetrahydro-2H-pyran-2-yl)oxy)decanal (c9). Thus, the title compound was obtained as a white solid weighing 4.07 g. (Yield: 68%)

$^1$H-NMR (270 MHz, CDCl$_3$) δ: 9.35 (1H, brd. s), 9.19 (1H, brd. s), 5.95 (1H, t, J=7.9 Hz), 4.63 (1H, brd. s), 3.89-3.70 (2H, m), 3.56-3.41 (2H, m), 2.56-2.18 (2H, m), 1.83-1.31 (20H, m).

⟨Step 2⟩ [Synthesis of 5-(10-hydroxydecylidene)-2-thioxoimidazolidin-4-one (c11)]

The procedures in Step 2 of the method described in Production Example 8 were repeated except that 5-(10-((tetrahydro-2H-pyran-2-yl)oxy)decylidene)-2-thioxoimidazolidin-4-one (c10) obtained in Step 1 described above was used. Thus, the title compound was obtained as a white solid weighing 2.91 g. (Yield: 94%)

$^1$H-NMR (270 MHz, CDCl$_3$) δ: 11.95 (2H, brd. s), 5.64 (1H, t, J=8.2 Hz), 4.29 (1H, brd. s), 3.30 (2H, m), 2.30-2.22 (2H, m), 1.39-1.24 (14H, m).

⟨Step 3⟩ [Synthesis of 10-(5-oxo-2-thioxoimidazolidin-4-ylidene)decyl methacrylate (a25)]

The procedures in Step 3 of the method described in Production Example 8 were repeated except that 5-(10-hydroxydecylidene)-2-thioxoimidazolidin-4-one (c11) obtained in Step 2 described above was used. Thus, the title compound was obtained as a light yellow solid weighing 1.15 g. (Yield: 26%)

$^1$H-NMR (270 MHz, DMSO-d$_6$) δ: 12.0 (2H, brd. s), 5.99 (1H, s), 5.64 (1H, s), 5.64 (1H, m), 4.06 (2H, t, J=6.4 Hz), 2.25 (2H, m), 1.86 (3H, s), 1.50-1.66 (2H, m), 1.15-1.47 (12H, m).

[Production Example 11] [Synthesis of 6-(5-oxo-2-thioxoimidazolidin-4-yl)hexyl methacrylate (a20)]

[Chem. 23]

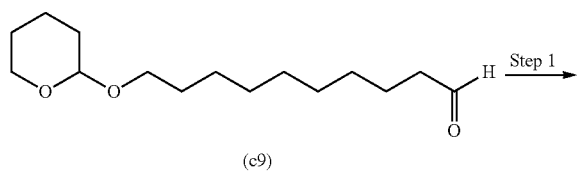
(c9)

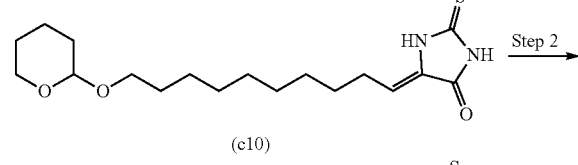
(c10)

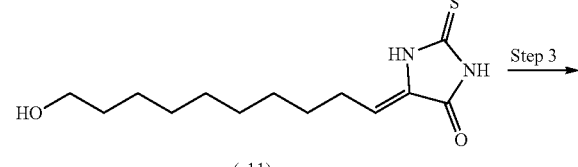
(c11)

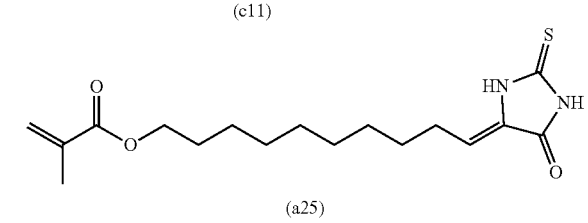
(a25)

[Chem. 24]

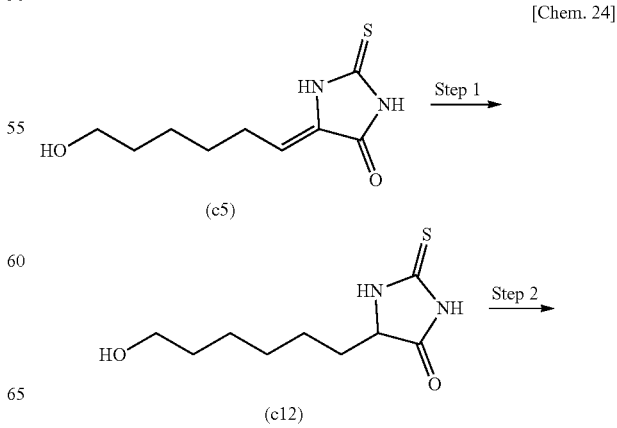
(c5)

(c12)

-continued

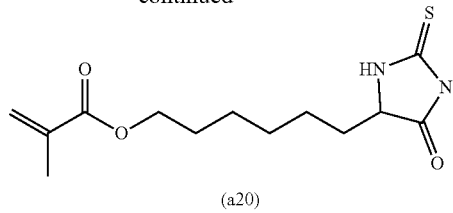

(a20)

⟨ Step 1 ⟩ [Synthesis of 5-(6-hydroxyhexyl)-2-thioxoimidazolidin-4-one (c12)]

In an air atmosphere, a 300 ml recovery flask was loaded with 3.60 g (16.8 mmol) of 5-(6-hydroxyhexylidene)-2-thioxoimidazolidin-4-one (c5), and 100 ml of ethanol was added to give a solution. A solution of 1.27 g (33.6 mmol) of sodium borohydride in 20 ml of ethanol was added dropwise to the flask at room temperature, and the mixture was stirred at room temperature for 1.5 hours. 1 M hydrochloric acid was added to the reaction solution in the flask until pH test paper showed acidity. The mixture was then stirred for 30 minutes. After 100 ml of water was added to the mixture in the flask, the mixture was extracted with ethyl acetate (100 ml×3 times). The extracts were combined, dried over magnesium sulfate, and concentrated under reduced pressure. The resultant residue was purified by washing with 20 ml of ethyl acetate and 20 ml of hexane. Thus, the title compound was obtained as a white solid weighing 1.99 g. (Yield: 55%)

$^1$H-NMR (270 MHz, DMSO-$d_6$) δ: 11.6 (1H, s), 10.0 (1H, s), 4.34 (1H, t, J=5.1 Hz), 4.18 (1H, t, J=5.4 Hz), 3.24-3.46 (2H, m) 1.10-1.75 (10H, m).

⟨ Step 2 ⟩ [Synthesis of 6-(5-oxo-2-thioxoimidazolidin-4-yl)hexyl methacrylate (a20)]

The procedures in Step 3 of the method described in Production Example 8 were repeated except that 5-(6-hydroxyhexyl)-2-thioxoimidazolidin-4-one (c12) obtained in Step 1 described above was used. Thus, the title compound was obtained as a white solid weighing 0.826 g. (Yield: 27%)

$^1$H-NMR (270 MHz, DMSO-$d_6$) δ: 11.6 (1H, brd. s), 10.0 (1H, brd. s), 6.00 (1H, s), 5.65 (1H, s), 4.18 (1H, t, J=5.8 Hz), 4.07 (2H, t, J=5.8 Hz), 1.87 (3H, s), 1.46-1.76 (4H, m), 1.14-1.21 (6H, m).

[Production Example 12] [Synthesis of 10-(5-oxo-2-thioxoimidazolidin-4-yl)decyl methacrylate (a24)]

[Chem. 25]

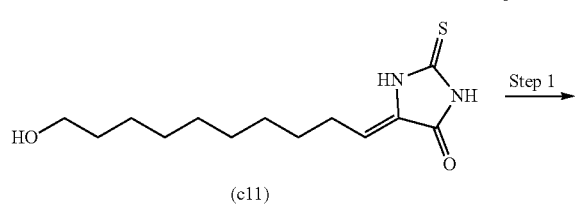

(c11)

-continued

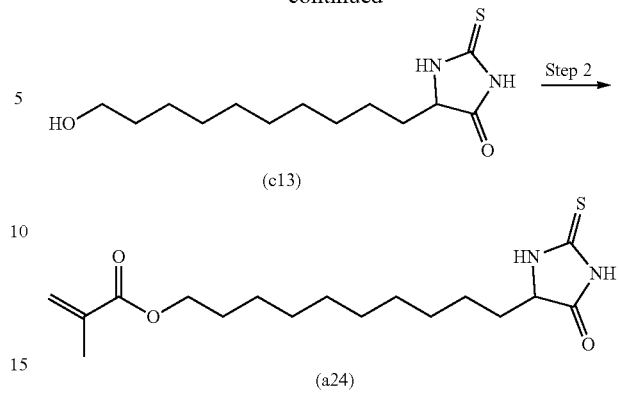

⟨ Step 1 ⟩ [Synthesis of 5-(10-hydroxydecyl)-2-thioxoimidazolidin-4-one (c13)]

Procedures in accordance with Step 1 of the method described in Production Example 11 were conducted using 5-(10-hydroxydecylidene)-2-thioxoimidazolidin-4-one (c11) synthesized in Production Example 10. Thus, the title compound was obtained as a white solid weighing 2.37 g. (Yield: 81%)

$^1$H-NMR (270 MHz, DMSO-$d_6$) δ: 11.6 (1H, brd. s), 10.0 (1H, brd. s), 4.29 (1H, m), 4.17 (1H, t, J=5.4 Hz), 3.18-3.53 (2H, m), 1.12-1.76 (18H, m).

⟨ Step 2 ⟩ [Synthesis of 10-(5-oxo-2-thioxoimidazolidin-4-yl) decyl methacrylate (a24)]

The procedures in Step 3 of the method described in Production Example 8 were repeated except that 5-(10-hydroxydecyl)-2-thioxoimidazolidin-4-one (c13) obtained in Step 1 described above was used. Thus, the title compound was obtained as a white solid weighing 0.584 g. (Yield: 20%)

$^1$H-NMR (270 MHz, DMSO-$d_6$) δ: 11.6 (1H, brd. s), 10.0 (1H, brd. s), 6.00 (1H, s), 5.65 (1H, s), 4.17 (1H, t, J=6.4 Hz), 4.07 (2H, t, J=5.6 Hz), 1.86 (3H, s), 1.46-1.83 (4H, m), 1.17-1.38 (14H, m).

Abbreviations

The following abbreviations were used.

⟨ Radically Polymerizable Monomers ⟩
MMA: Methyl methacrylate
4-META: 4-Methacryloyloxyethyl trimellitic acid anhydride
MDP: 10-Methacryloyloxydecyl acid phosphate
UDMA: 2,2,4-Trimethylhexamethylene bis(2-carbamoyloxyethyl) dimethacrylate
GDMA: Glycerol dimethacrylate ⟨ Silane coupling agent ⟩
2-TMSPMA: γ-Methacryloxypropyltrimethoxysilane ⟨ Filler ⟩
Fine silica: R812 (manufactured by NIPPON AEROSIL Co., Ltd.)

⟨ Polymerization Initiators ⟩
CQ: Camphorquinone
DTMPO: Diphenyl(2,4,6-trimethylbenzoyl)phosphine oxide ⟨Reducing Compounds⟩
NPG: N-Phenylglycine
TSNa: Sodium toluenesulfinate
Na$_2$SO$_3$: Sodium sulfite
⟨Organic Solven⟩
Isopropyl alcohol
⟨Sulfur-Containing Compound⟩
VBATDT: 6-(4-Vinylbenzyl-n-propyl)amino-1,3,5-triazine-2,4-dithione (tPSA=about 40 Å$^2$, C log P value=about 2.4)

[Chem. 26]

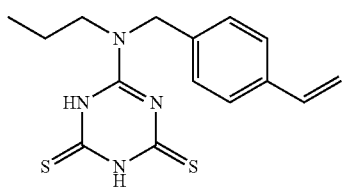

Example 1

2.6 Parts of 2-THPEM and 97.4 parts of acetone were mixed together to give a mixture.

Examples 2 to 31 and Comparative Examples 1 to 6

Solutions were obtained by adding the sulfur-containing compound of the amount described in Table 1 or Table 1a to the amount described in Table 1 or Table 1a of the organic solvent or the radically polymerizable monomer.

[Solubility Evaluation]

The solutions obtained were stirred with a magnetic stirrer for 0.5 hours and were then visually inspected for the presence of insolubles. The solutions were evaluated as ○ when the solution was transparent and free from insolubles, as Δ when the solution was turbid but free from insolubles, and as x when insolubles were present. The solubility evaluations in Tables 3 to 6 are also based on the same criteria.

TABLE 1

| | | | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|---|---|
| Formulations | Radically polymerizable monomer | MMA | | | 97.4 | | | 97.4 | | | 97.4 | | |
| | Organic solvents | Acetone | 97.4 | | | 97.4 | | 97.4 | | | | 97.4 | |
| | | IPA | | 97.4 | | | 97.4 | | | 97.4 | | | 97.4 |
| | Sulfur-containing compounds | 2-THPEM | 2.6 | 2.6 | 2.6 | | | | | | | | |
| | | 4-THPBM | | | | 2.6 | 2.6 | 2.6 | | | | | |
| | | 6-THPHM | | | | | | | 2.6 | 2.6 | 2.6 | | |
| | | 10-THPDM | | | | | | | | | | 2.6 | 2.6 |
| | | VBATDT | | | | | | | | | | | |
| Evaluation | Solubility | | ○ | ○ | ○ | ○ | ○ | ○ | ○ | ○ | ○ | ○ | ○ |
| | | | Ex. 12 | Ex. 13 | Ex. 14 | Ex. 15 | Ex. 16 | Comp. Ex. 1 | Comp. Ex. 2 | Comp. Ex. 3 | Comp. Ex. 4 | Comp. Ex. 5 | |
| Formulations | Radically polymerizable monomer | MMA | 97.4 | | | 99.35 | | | | 99.35 | | | |
| | Organic solvents | Acetone | | 99.35 | | | 80.0 | 97.4 | | | 99.5 | 80.0 | |
| | | IPA | | | 99.35 | | | | 99.35 | | | | |
| | Sulfur-containing compounds | 2-THPEM | | | | | | | | | | | |
| | | 4-THPBM | | | | | | | | | | | |
| | | 6-THPHM | | | | | | | | | | | |
| | | 10-THPDM | 2.6 | 0.65 | 0.65 | 0.65 | 20.00 | | | | | | |
| | | VBATDT | | | | | | 2.6 | 0.65 | 0.65 | 0.5 | 20.0 | |
| Evaluation | Solubility | | ○ | ○ | ○ | ○ | ○ | ○ | x | x | ○ | x | |

The unit of the amounts of the components is parts by mass.

TABLE 1a

| | | | Ex. 17 | Ex. 18 | Ex. 19 | Ex. 20 | Ex. 21 | Ex. 22 | Ex. 23 | Ex. 24 |
|---|---|---|---|---|---|---|---|---|---|---|
| Formulations | Radically polymerizable monomer | MMA | 97.4 | | | 97.4 | | 97.4 | | |
| | Organic solvents | Acetone | | 90 | | | 80 | | | 80 |
| | | IPA | | | 99.35 | | | 97.4 | | |
| | Sulfur-containing compounds | a21 | 2.6 | 10 | 0.65 | | | | | |
| | | a23 | | | | 2.6 | 20 | 2.6 | | |
| | | a25 | | | | | | | 2.6 | 20 |
| | | a20 | | | | | | | | |
| | | a24 | | | | | | | | |
| | | VBATDT | | | | | | | | |
| Evaluation | Solubility | | ○ | ○ | ○ | ○ | ○ | ○ | ○ | ○ |

TABLE 1a-continued

| | | Ex. 25 | Ex. 26 | Ex. 27 | Ex. 28 | Ex. 29 | Ex. 30 | Ex. 31 | Comp. Ex. 6 |
|---|---|---|---|---|---|---|---|---|---|
| Formulations | Radically polymerizable monomer | | | | | | | | |
| | MMA | | 97.4 | | | 97.4 | | | |
| | Organic solvents | | | | | | | | |
| | Acetone | | | 80 | | | 80 | | 90 |
| | IPA | 97.4 | | | 97.4 | | | 97.4 | |
| | Sulfur-containing compounds | | | | | | | | |
| | a21 | | | | | | | | |
| | a23 | | | | | | | | |
| | a25 | 2.6 | | | | | | | |
| | a20 | | 2.6 | 20 | 2.6 | | | | |
| | a24 | | | | | 2.6 | 20 | 2.6 | |
| | VBATDT | | | | | | | | 10 |
| Evaluation | Solubility | ○ | ○ | ○ | ○ | ○ | ○ | ○ | x |

The unit of the amounts of the components is parts by mass.

The results described in Table 1 and Table 1a show that VBATDT had low solubility with respect to IPA and MMA, while the compounds from Production Examples exhibited high solubility and were easily dissolved into both organic solvents, acetone and IPA, and also showed high solubility with respect to MMA which is a typical methacrylate monomer. When added to acetone at a concentration of 20 mass %, VBATDT generated insolubles while 10-THPDM was dissolved completely.

Example 1A

A composition was obtained by mixing 0.65 parts of 10-THPDM with 99.35 parts of acetone.

Examples 1B to 10B, 1C to 4C, and 1D to 3D

Comparative Examples 1 Å, 1B, 1C to 3C, 1D and 2D

Compositions were obtained by mixing the components in the amounts shown in Tables 3 to 6.

[Metal Test Pieces for Adhesion Test]

Table 2 describes the dental pure metals/alloys for adhesion test and the sizes of metal test pieces.

[Table 2]

TABLE 2

| Metal test pieces | Product names | Test piece size (mm) |
|---|---|---|
| Pure silver | — | 6 φ × 6.5 |
| Pure platinum | — | 10 φ × 6.5 |
| Pure palladium | — | 6 φ × 6.5 |
| Pure copper | — | 10 φ × 6.5 |
| Gold alloy | Casting Gold MC type IV | 7 φ × 6.5 |
| Gold silver palladium alloy | Castwell MC | 7 φ × 6.5 |

[Method a of Testing Adhesion with Respect to Dental Pure Metals and Alloys]

While pouring water to the metal test pieces, their bonding surfaces were sequentially polished with silicon carbide abrasive papers of up to #2000 grade (#800, 1200, 1500 and 2000) and were specular finished with alumina microparticles. The specular bonding surfaces were brush-coated with 25 μg each of the compositions prepared in Example and Comparative Example. After 20 minutes, the surface-treated metal test pieces were ultrasonically cleaned in a large amount of acetone for 20 minutes. The metal test pieces were continuously stored in the acetone for 24 hours while ensuring that the acetone would not volatilize.

After the storage, the surface-treated metal test pieces were ultrasonically cleaned again for 30 minutes prior to the adhesion test, and were air-dried immediately before use. To define the bonding area, a cellophane tape perforated with a diameter of 5 mm was attached to the bonding surface of the surface-treated metal test pieces, and the metal test pieces of the same type and the same size were butt-bonded to each other. The adhesive material used was Catalyst V and the polymer powder (clear) of SUPERBOND (manufactured by SUN MEDICAL CO., LTD.), and the monomer solution used was methyl methacrylate (ACRYESTER M). The bonding operation was conducted by a brush-on technique. The specimens composed of the metal test pieces bonded together were allowed to stand in a thermostatic chamber at 37° C. for 3 days and were then immersed in water at 37° C. for 24 hours.

To evaluate the adhesion durability, the specimens were subjected to a thermal cycle test consisting of 2,000 cycles of alternate 1-minute immersions in constant temperature water baths at 4° C. and 60° C. The specimens after the thermal cycle test were kept wet and were tested with an autograph (SHIMADZU CORPORATION) at a crosshead speed of 2 mm/min to measure the tensile break strength. The bond strength (MPa) was calculated from the area. The results of five samples were averaged.

[Method B of Testing Adhesion with Respect to Dental Alloys]

While pouring water to Casting Gold MC type IV or Castwell MC, the bonding surface of the metal test piece was sequentially polished and finished with silicon carbide abrasive papers of up to #2000 grade (#600, 1000 and 2000). The polished metal test pieces were ultrasonically cleaned in water for 10 minutes and were air-dried. To define the bonding area, a cellophane tape perforated with a diameter of 4.8 mm was attached to the bonding surface. The bonding surfaces were coated with 25 μg each of the compositions prepared in Examples and Comparative Examples and were allowed to stand for 20 seconds. The surfaces were then dried by air blowing until the composition lost fluidity. In the case where the composition contained a polymerization initiator, 460 nm wavelength light was applied from an LED illuminator at about 1000 mW/cm$^2$ for 5 seconds. Thereafter, SUPERBOND (manufactured by SUN MEDICAL CO., LTD.) as an adhesive resin was applied by a brush-on technique onto the bonding surface coated with the composition, and a stainless steel rod that had been sandblasted with 50 μm alumina was bonded thereto.

The specimens composed of the stainless steel rod and the metal test piece bonded together were allowed to stand at room temperature for 30 minutes. To evaluate the adhesion durability, the specimens were subjected to a thermal cycle test consisting of 5,000 cycles of alternate 20-second immersions in water at 5° C. and 55° C. The specimens after the thermal cycle test were kept wet and were tested with an autograph (SHIMADZU CORPORATION) at a crosshead speed of 2 mm/min to measure the tensile break strength. The bond strength (MPa) was calculated from the area. The results of five samples were averaged.

[Method C of Testing Adhesion with Respect to Bovine Teeth]

The bond strength with respect to bovine enamel or dentin was tested in the following manner.

Fresh bovine mandibular anterior teeth were removed and were frozen in water for temporal storage. In the preparation of adhesion test samples, the thawed bovine teeth were ground with waterproof emery papers of up to #180 grade using rotational polishing machine ECOMET-III (manufactured by BUEHLER) while pouring water and applying finger pressure so as to expose flat faces of enamel or dentin. The bovine teeth that had been ground were dried with an air gun. Immediately thereafter, a cellophane tape having a circular aperture with a diameter of 4.8 mm was attached to define the bonding area. The tooth substance surfaces of the test pieces were subjected to the adhesion test. Specifically, 25 μg each of the compositions prepared in Examples and Comparative Examples were applied to the defined areas of the tooth surfaces and were allowed to stand for 20 seconds. The surfaces were then dried by air blowing until the composition lost fluidity. In the case where the composition contained a polymerization initiator, 460 nm wavelength light was applied from an LED illuminator at about 1000 mW/cm² for 5 seconds. Thereafter, SUPERBOND (manufactured by SUN MEDICAL CO., LTD.) was applied to the surface by a brush-on technique, and an acrylic rod 5 mm in diameter was allowed to stand thereon. The specimens composed of the acrylic rod and the test piece bonded together were allowed to stand at room temperature for 30 minutes and were immersed in water at 37° C. for 24 hours. The specimens were then tested with an autograph (SHIMADZU CORPORATION) at a crosshead speed of 2 mm/min to measure the tensile break strength. The bond strength (MPa) was calculated from the area. The results of five samples were averaged.

[Method D of Testing Adhesion with Respect to Ceramics]

The bond strength with respect to ceramics was tested in the following manner.

Industrial zirconium oxide or porcelain (AAA) was used as test pieces. The bonding surface thereof was sequentially polished and finished with silicon carbide abrasive papers of up to #2000 grade (#600, 1000 and 2000). The polished ceramic test pieces were ultrasonically cleaned in water for 10 minutes and were air-dried. To define the bonding area, a tape perforated with a diameter of 4.8 mm was attached to the bonding surface. The bonding surfaces were coated with 25 μg each of the compositions prepared in Examples and Comparative Examples and were allowed to stand for 20 seconds. The surfaces were then dried by air blowing until the composition lost fluidity. In the case where the composition contained a polymerization initiator, 460 nm wavelength light was applied from an LED illuminator at about 1000 mW/cm² for 5 seconds. Thereafter, SUPERBOND (manufactured by SUN MEDICAL CO., LTD.) as an adhesive resin was applied by a brush-on technique, and a stainless steel rod that had been sandblasted with 50 μm alumina was bonded thereto.

The specimens composed of the stainless steel rod and the ceramic test piece bonded together were allowed to stand at room temperature for 30 minutes. To evaluate the adhesion durability, the specimens were subjected to a thermal cycle test consisting of 5,000 cycles of alternate 20-second immersions in water at 5° C. and 55° C. The specimens after the thermal cycle test were kept wet and were tested with an autograph (SHIMADZU CORPORATION) at a crosshead speed of 2 mm/min to measure the tensile break strength. The bond strength (MPa) was calculated from the area. The results of five samples were averaged.

[Adhesion Tests]

The compositions obtained in Examples and Comparative Examples were tested based on the adhesion test methods A, B, C and D described above to measure the bond strength with respect to the various adherends. The results are described in Tables 3 to 6.

The bond strength with respect to the various adherends was compared between the adhesive compositions containing the compound (A) of the present invention, and conventional adhesive materials. The results have shown that the compositions of Examples exhibit excellent adhesion durability with respect to noble metals and alloys thereof, and have also confirmed that the compounds (A) of the present invention do not adversely affect the adhesion to the tooth substances.

TABLE 3

|  |  |  | Ex. 1A | Comp. Ex. 1A |
|---|---|---|---|---|
| Formulations | Organic solvent | Acetone | 99.35 | 99.5 |
|  | Sulfur-containing | 10-THPDM | 0.65 |  |
|  | compounds | VBATDT |  | 0.5 |
| Evaluations | Solubility |  | ◯ | ◯ |
|  | Adhesion test method |  | A | A |
|  | Adhesion to metals | Pure silver | 49 | 39 |
|  | Bond strength (MPa) | Pure platinum | 55 | 48 |
|  |  | Pure palladium | 47 | 0 |
|  |  | Pure copper | 51 | 0 |
|  |  | Gold alloy | 48 | 46 |
|  |  | Gold silver palladium alloy | 48 | 46 |

The unit of the amounts of the components is parts by mass.

TABLE 4

| | | Ex. 1B | Ex. 2B | Ex. 3B | Ex. 4B | Ex. 5B | Ex. 6B | Ex. 7B | Ex. 8B | Ex. 9B | Ex. 10B | Comp. Ex. 1B |
|---|---|---|---|---|---|---|---|---|---|---|---|---|
| Formulations | Radically polymerizable monomers | MMA | | | 97.4 | | 99.35 | | | 5.00 | 33.00 | 5.00 | |
| | | 4-META | | | | | | | 15.00 | 30.00 | 10.00 | 10.00 | |
| | | MDP | | | | | | | | | | 10.00 | |
| | | UDMA | | | | | | | | 30.00 | 20.00 | 20.00 | |
| | | GDMA | | | | | | | | | | 10.00 | |
| | Silane coupling agent | 2-TMSPMA | | | | | | | | | 7.00 | | |
| | Organic solvents | Acetone | 97.4 | | | 99.35 | | | 41.35 | 22.60 | 20.77 | 18.15 | 100.0 |
| | | IPA | | 97.4 | | | 99.35 | | | | | | |
| | Filler | Fine silica | | | | | | | | | | 10.00 | |
| | Purified water | | | | | | | | 40.00 | 10.00 | 7.00 | 10.00 | |
| | Polymerization initiators | CQ | | | | | | | | 0.10 | 0.10 | 0.10 | |
| | | DTMPO | | | | | | | | 0.10 | 0.10 | 0.10 | |
| | Reducing compounds | NPG | | | | | | | | 0.75 | 0.80 | 3.00 | |
| | | TSNa | | | | | | | | 0.75 | 0.80 | 3.00 | |
| | | Na2SO3 | | | | | | | 3.00 | | | | |
| | Sulfur-containing compounds | 10-THPDM | 2.6 | 2.6 | 2.6 | 0.65 | 0.65 | 0.65 | 0.65 | 0.65 | 0.43 | 0.65 | |
| | | VBATDT | | | | | | | | | | | 0.0 |
| Evaluations | Solubility | | ○ | ○ | ○ | ○ | ○ | ○ | ○ | ○ | ○ | ○ | — |
| | Adhesion test method | | B | B | B | B | B | B | B | B | B | B | B |
| | Adhesion to metals (MPa) Bond strength | Gold alloy | 10 | 14 | 8 | na | na | na | na | na | 25 | 11 | 0 |
| | | Gold silver palladium alloy | 15 | 11 | 20 | 26 | 14 | 11 | 13 | 23 | 28 | 12 | 0 |

The unit of the amounts of the components is parts by mass.
na: Not evaluated

TABLE 5

| | | | Ex. 1C | Ex. 2C | Ex. 3C | Ex. 4C | Comp. Ex. 1C | Comp. Ex. 2C | Comp. Ex. 3C |
|---|---|---|---|---|---|---|---|---|---|
| Formulations | Radically polymerizable monomers | MMA | | 5.00 | 33.00 | 5.00 | | 5.00 | 5.00 |
| | | 4-META | 15.00 | 30.00 | 10.00 | 10.00 | 15.00 | 30.00 | 10.00 |
| | | MDP | | | | 10.00 | | | 10.00 |
| | | UDMA | | 30.00 | 20.00 | 20.00 | | 30.00 | 20.00 |
| | | GDMA | | | | 10.00 | | | 10.00 |
| | Silane coupling agent | 2-TMS PMA | | | | 7.00 | | | |
| | Organic solvents | Acetone | 41.35 | 22.65 | 20.77 | 18.15 | 42.00 | 23.30 | 18.80 |
| | | IPA | | | | | | | |
| | Filler | Fine silica | | | | 10.00 | | | 10.00 |
| | Purified water | | 40.00 | 10.00 | 7.00 | 10.00 | 40.00 | 10.00 | 10.00 |
| | Polymerization initiators | CQ | | 0.10 | 0.10 | 0.10 | | 0.10 | 0.10 |
| | | DTMPO | | 0.10 | 0.10 | 0.10 | | 0.10 | 0.10 |
| | Reducing compounds | NPG | | 0.75 | 0.80 | 3.00 | | 0.75 | 3.00 |
| | | TSNa | | 0.75 | 0.80 | 3.00 | | 0.75 | 3.00 |
| | | Na2SO3 | 3.00 | | | | 3.00 | | |
| | Sulfur-containing compounds | 10-THPDM | 0.65 | 0.65 | 0.43 | 0.65 | | | |
| | | VBATDT | | | | | 0.0 | 0.0 | 0.0 |
| Evaluations | Solubility | | ○ | ○ | ○ | ○ | ○ | ○ | ○ |
| | Adhesion test method | | C | C | C | C | C | C | C |
| | Adhesion to tooth substances Bond strength (MPa) | Bovine enamel | 13 | 9 | 6 | 6 | 9 | 9 | 7 |
| | | Bovine dentin | 16 | 8 | 8 | 7 | 13 | 8 | 9 |

The unit of the amounts of the components is parts by mass.

TABLE 6

| | | | Ex. 1D | Ex. 2D | Ex. 3D | Comp. Ex. 1D | Comp. Ex. 2D |
|---|---|---|---|---|---|---|---|
| Formulations | Radically polymerizable monomers | MMA | 5.00 | 35.00 | 33.00 | 5.00 | 35.00 |
| | | 4-META | 10.00 | | 10.00 | 10.00 | |
| | | MDP | 10.00 | 1.50 | | 10.00 | 1.50 |
| | | UDMA | 20.00 | | 20.00 | 20.00 | |
| | | GDMA | 10.00 | | | 10.00 | |
| | Silane coupling agent | 2-TMS PMA | | 10.00 | 7.00 | | 10.00 |

TABLE 6-continued

|  |  | Ex. 1D | Ex. 2D | Ex. 3D | Comp. Ex. 1D | Comp. Ex. 2D |
|---|---|---|---|---|---|---|
| Organic solvents | Acetone | 18.15 |  | 20.77 | 18.80 |  |
|  | IPA |  | 53.40 |  |  | 53.40 |
| Filler | Fine silica | 10.00 |  |  | 10.00 |  |
| Purified water |  | 10.00 |  | 7.00 | 10.00 |  |
| Polymerization initiators | CQ | 0.10 |  | 0.10 | 0.10 |  |
|  | DTMPO | 0.10 |  | 0.10 | 0.10 |  |
| Reducing compounds | NPG | 3.00 |  | 0.80 | 3.00 |  |
|  | TSNa | 3.00 |  | 0.80 | 3.00 |  |
|  | Na2SO3 |  |  |  |  |  |
| Sulfur-containing compounds | 10-THPDM | 0.65 | 0.10 | 0.43 |  |  |
|  | VBATDT |  |  |  | 0.0 | 0.10 |
| Evaluations | Solubility | ○ | ○ | ○ | ○ | ○ |
|  | Adhesion test method | D | D | D | D | D |
| Adhesion to ceramics Bond strength (MPa) | Zirconium oxide | 8 | 28 | 5 | 2 | 24 |
|  | Porcelain | — | 20 | 29 | — | 18 |

The unit of the amounts of the components is parts by mass.

The invention claimed is:

1. A compound (A) represented by the formula (1):

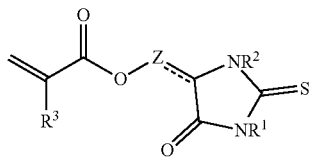
(1)

wherein
R$^1$ is a hydrogen atom or an alkali metal atom,
R$^2$ is a hydrogen atom or an alkali metal atom,
R$^3$ is a hydrogen atom or a methyl group,
Z is a divalent or trivalent organic group, and the lines consisting of a solid line and a broken line bonded to Z represent a single bond or a double bond,
provided that when R$^1$ and R$^2$ are a hydrogen atom, and R$^3$ is a methyl group, Z is not a trivalent organic group including 1,4-phenylene group,
the compound (A) is not a compound represented by following formula:

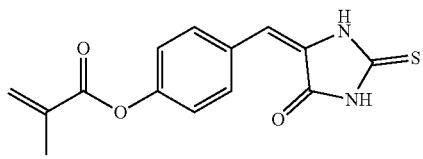 [SMILES: C=C(C)C(=O)Oc1ccc(/C=C2/NC(=S)NC2=O)cc1]

the divalent or trivalent organic group Z in the formula (1) includes one or more groups selected from divalent groups represented by formula (Z1), ether bonds, 1,4-phenylene groups, 1,4-cyclohexylene groups and divalent linear saturated hydrocarbon groups,

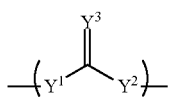
(Z1)

wherein Y$^1$ and Y$^2$ are each independently an oxygen atom, a divalent group represented by —CH$_2$— or a divalent group represented by —NH—, and Y$^3$ is an oxygen atom or a sulfur atom.

2. The compound (A) according to claim 1, wherein the molecular weight is 200 to 600.

3. The compound (A) according to claim 1, wherein the topological polar surface area (tPSA) is not less than 50.00 Å$^2$.

4. The compound (A) according to claim 3, wherein the C log P value is not less than −5.000.

5. The compound (A) according to claim 1, wherein the divalent or trivalent organic group Z in the formula (1) is a C6-C20 linear saturated hydrocarbon group or a C6-C20 group having —O—C(=O)—CH$_2$—.

6. A cured product obtained by curing an adhesive composition comprising a compound (A) represented by the formula (1) to a metal including a noble metal, a tooth substance or a ceramic:

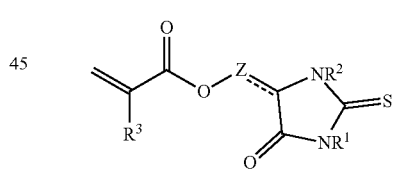
(1)

wherein R$^1$ is a hydrogen atom or an alkali metal atom,
R$^2$ is a hydrogen atom or an alkali metal atom,
R$^3$ is a hydrogen atom or a methyl group,
Z is a divalent or trivalent organic group, and the lines consisting of a solid line and a broken line bonded to Z represent a single bond or a double bond.

7. The compound (A) according to claim 1, wherein —C(=O)O— in the formula (1) is bonded to a CH$_2$ group in Z.

8. The compound (A) according to claim 1, wherein the divalent or trivalent organic group Z in the formula (1) includes one or more groups selected from divalent groups represented by formula (Z1), ether bonds, 1,4-cyclohexylene groups and divalent linear saturated hydrocarbon groups.

* * * * *